(12) United States Patent
Resnick et al.

(10) Patent No.: US 7,674,813 B2
(45) Date of Patent: Mar. 9, 2010

(54) HETEROCYCLIC SULFONAMIDE INHIBITORS OF BETA AMYLOID PRODUCTION CONTAINING AN AZOLE

(75) Inventors: Lynn Resnick, Parlin, NJ (US); Donna M. Huryn, Allentown, NJ (US); Joan E. Sabalski, Hamilton, NJ (US); Joshua D. Berkowitz, Newtown, PA (US); Anthony Frank Kreft, Langhorne, PA (US); Dennis Martin Kubrak, Philadelphia, PA (US); Thomas Joseph Caggiano, Morrisville, PA (US); Koi Michele Morris, Plainsboro, NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 12/142,306

(22) Filed: Jun. 19, 2008

(65) Prior Publication Data

US 2008/0249150 A1 Oct. 9, 2008

Related U.S. Application Data

(62) Division of application No. 11/035,005, filed on Jan. 13, 2005, now Pat. No. 7,399,778.

(60) Provisional application No. 60/537,086, filed on Jan. 16, 2004.

(51) Int. Cl.
*A01N 43/50* (2006.01)
*A01N 43/56* (2006.01)
*C07D 231/00* (2006.01)

(52) U.S. Cl. .................................. 514/403; 548/373.1
(58) Field of Classification Search ................ 514/403; 548/373.1
See application file for complete search history.

(56) References Cited

U.S. PATENT DOCUMENTS

| | | |
|---|---|---|
| 5,593,846 A | 1/1997 | Schenk et al. |
| 5,703,129 A | 12/1997 | Felsenstein et al. |
| 5,741,794 A | 4/1998 | Bowles et al. |
| 5,852,007 A | 12/1998 | Chatterjee |
| 6,218,418 B1 | 4/2001 | Pevarello et al. |
| 6,248,775 B1 | 6/2001 | Vazquez et al. |
| 6,610,734 B2 | 8/2003 | Kreft et al. |
| 6,657,070 B2 | 12/2003 | Resnick |
| 6,878,742 B2 | 4/2005 | Kreft et al. |
| 7,300,951 B2 | 11/2007 | Kreft et al. |
| 7,399,778 B2 | 7/2008 | Resnick et al. |
| 2005/0196813 A1 | 9/2005 | Kreft et al. |

FOREIGN PATENT DOCUMENTS

| | | |
|---|---|---|
| EP | 652009 | 5/1995 |
| EP | 1088821 | 4/2001 |
| WO | WO 98/22493 | 5/1998 |
| WO | WO-9912910 * | 3/1999 |
| WO | WO 00/50391 | 8/2000 |
| WO | WO 01/23379 | 4/2001 |
| WO | WO 01/27091 | 4/2001 |
| WO | WO 01/27108 | 4/2001 |
| WO | WO 01/70677 | 9/2001 |
| WO | WO 01/94318 | 12/2001 |
| WO | WO 02/057252 | 7/2002 |
| WO | WO 03/050062 | 6/2003 |

OTHER PUBLICATIONS

Morissette et al., Advanced Drug Delivery Reviews, 2004, 56, 275-300.*
Patani et al., Chem Rev, 1996, vol. 96 (8), pp. 3147-3176.*
Augelli-Szafran, "β-amyloid as a target for Alzheimer's disease therapy", Annual Reports in Medicinal Chemistry, 34:21-30 (1999).
Dodart, "The β-amyloid precursor protein and its derivatives: from biology to learning and memory processes", Rev Neurosci, 11(2-3):75-93 (2000).
Dovey, "Functional gamma-secretase inhibitors reduce β-amyloid peptide levels in brain", J NeuroChem, 76(1):173-181 (Jan. 2001).
Esler, "Transition-state analogue inhibitors of gamma-secretase bind directly to presenilin-1", Nat Cell Biol, 2(7):428-434 (Jul. 2000).
Findeis, "Modified-peptide inhibitors of amyloid β-peptide polymerization", BioChem, 38(21):6791-6800 (May 1999).
Ghosh, "Design of Potent Inhibitors for Human Brain Memapsin 2 (β-Secretase)", J Am Chem Soc, 122(14):3522-3523 (Apr. 12, 2000).
Goate, "Monogenetic determinants of Alzheimer's disease: APP mutations", Cell Mol Life Sci, 54(4):897-901 (Sep. 1998).

(Continued)

*Primary Examiner*—Golam M. M. Shameem
*Assistant Examiner*—Susannah Chung
(74) *Attorney, Agent, or Firm*—Scott K. Larsen; Howson & Howson LLP

(57) ABSTRACT

Compounds useful for lowering beta amyloid levels are provided. The compounds have the structure of formula Ia:

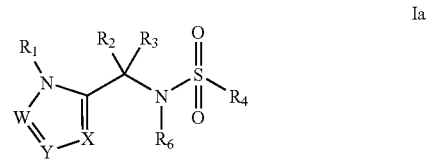

wherein, $R_1$ is lower alkyl, substituted lower alkyl, phenyl, substituted phenyl, benzyl, substituted benzyl, benzyloxy, substituted benzyloxy, or $SO_2R_5$; $R_5$ is phenyl, substituted phenyl, heterocycle, substituted heterocycle, alkyl, or substituted alkyl; $R_2$ is lower alkyl, substituted lower alkyl, $CF_3$, alkenyl, substituted alkenyl, alkynyl, substituted alkynyl, phenyl, substituted phenyl, or cycloalkyl; $R_3$ is hydrogen, lower alkyl, or substituted lower alkyl; $R_4$ is phenyl, substituted phenyl, heterocycle, substituted heterocycle, thiophene, or substituted thiophene; $R_6$ is hydrogen, lower alkyl, substituted lower alkyl, $CF_3$, alkenyl, substituted alkenyl, alkynyl, substituted alkynyl, phenyl, substituted phenyl, cycloalkyl, or substituted cycloalkyl; W, X and Y are independently $CR_7$ or N; and $R_7$ is hydrogen, halogen, lower alkyl, or substituted lower alkyl.

9 Claims, No Drawings

OTHER PUBLICATIONS

Josien, "Recent advances in the development of gamma-secretase inhibitors", Curr Opin Drug Disc Dev, 5(4):513-525 (Jul. 2002).

Larner, "Review—Central and peripheral nervous systems—Alzheimer's disease: Towards therapeutic manipulation of the amyloid precursor protein and amyloid peptides", Exp Opin Ther Patents, 7(10):1115-1127 (Oct. 1997).

Li, "Photoactivated-secretase inhibitors directed to the active site covalently label presenilin 1", Nature, 405(6787):689-694 (Jun. 8, 2000).

Li, "The amyloid precursor protein of Alzheimer disease in human brain and blood", J Leukocyte Biol, 66(4):567-574 (Oct. 1999).

Lu, "Indium-mediated organometallic reactions in aqueous media. Stereoselectivity in the crotylation of sulfonimines bearing a proximal chelating group", J Org Chem, 66(10):3467-3473 (May 18, 2001).

Moore, "Inhibition of β-amyloid formation as a therapeutic strategy", Exp Opin Ther Patents, 9(2):135-146 (Feb. 1999).

Naslund, "Correlation between elevated levels of amyloid β-peptide in the brain and cognitive decline", J Am Med Assoc, 283(12):1571-1577 (Mar. 22-29, 2000).

Olson, "Chapter 4. Secretase inhibitors as therapeutics for Alzheimer's disease", Ann Reports in Med Chem, 35:31 (2000).

Rishton, "Fenchylamine sulfonamide inhibitors of amyloid β peptide production by the gamma-secretase proteolytic pathway: potential small-molecule therapeutic agents for the treatment of Alzheimer's disease", J Med Chem, 43(12):2297-2299 (Jun. 15, 2000).

Roggo, "Inhibition of BACE, a promising approach to Alzheimer's disease therapy", Curr Top Med Chem, 2(4):359-370 (Apr. 2002).

Sabbagh, "β-amyloid and treatment opportunities for Alzheimer's disease", Alzheimer's Disease Review, 3:1-19 (1997).

Saha, "Novel antifungals based on 4-substituted imidazole: a combinatorial chemistry approach to lead discovery and optimization", Bioorg Med Chem Lett, 10(19):2175-2178 (Oct. 2, 2000).

Sinha, "Purification and cloning of amyloid precursor protein β-secretase from human brain", Nature, 402(6761):537-540 (Dec. 2, 1999).

Small, "Alzheimer's disease and the amyloid β protein: What is the role of amyloid?", J Neuro Chem, 73(2):443-449 (Aug. 1999).

Tung, "Design of substrate-based inhibitors of human β-secretase", J Med Chem, 45(2):259-262 (Jan. 17, 2002).

Varghese, "Alzheimer's disease: Recent advances on the amyloid hypothesis", Ann Reports Med Chem, 32:11-20 (1997).

* cited by examiner

HETEROCYCLIC SULFONAMIDE INHIBITORS OF BETA AMYLOID PRODUCTION CONTAINING AN AZOLE

CROSS-REFERENCE TO RELATED APPLICATIONS

This application is a divisional of U.S. patent application Ser. No. 11/035,005, filed Jan. 13, 2005, which claims the benefit of the priority of US Provisional Patent Application No. 60/537,086, filed Jan. 16, 2004, now abandoned.

BACKGROUND OF THE INVENTION

Alzheimer's disease (AD) is the most common form of dementia (loss of memory) in the elderly. The main pathological lesions of AD found in the brain consist of extracellular deposits of beta amyloid protein in the form of plaques and angiopathy and intracellular neurofibrillary tangles of aggregated hyperphosphorylated tau protein. Recent evidence has revealed that elevated beta amyloid levels in brain not only precede tau pathology but also correlate with cognitive decline. Further suggesting a causative role for beta amyloid in AD, recent studies have shown that aggregated beta amyloid is toxic to neurons in cell culture and has a detrimental effect on memory. This suggests that reducing beta amyloid levels is a viable therapeutic strategy for the treatment of AD.

Beta amyloid protein is composed mainly of 39-42 amino acid peptides and is produced from a larger precursor protein called amyloid precursor protein (APP) by the sequential action of the proteases beta and gamma secretase. Although rare, cases of early onset AD have been attributed to genetic mutations in APP that lead to an overproduction of either total beta amyloid protein or its more aggregation-prone 42 amino acid isoform. Furthermore, people with Down's Syndrome possess an extra chromosome that contains the gene that encodes APP and thus have elevated beta amyloid levels and invariably develop AD later in life.

One approach to the inhibition of beta amyloid production is to target the recently described beta secretase enzyme. Three groups have recently reported peptide-based beta secretase inhibitors. A second approach is to target gamma secretase the other enzyme involved in beta amyloid production. Although gamma secretase has not yet been fully characterized, recent evidence suggests that the presenilins may be gamma secretases. Several gamma secretase inhibitors have been designed based upon the amino acid sequence of the APP cleavage site. Importantly, a gamma secretase inhibitor DAPT (LY374973, AN37124) has been recently shown to reduce beta amyloid protein levels in mice brains in vivo after oral administration.

What are needed are compounds that are effective in lowering beta amyloid production.

SUMMARY OF THE INVENTION

The invention provides compounds of formula Ia, their pharmaceutical formulations, and their use in inhibiting beta amyloid production in patients susceptible to, or suffering from, AD or other diseases resulting from elevated levels of beta amyloid protein in the brain.

Other aspects and advantages of the present invention are described further in the following detailed description of the preferred embodiments thereof.

DETAILED DESCRIPTION OF THE INVENTION

The present invention provides compounds of formula Ia and pharmaceutically acceptable salts and/or hydrates or prodrugs thereof, wherein:

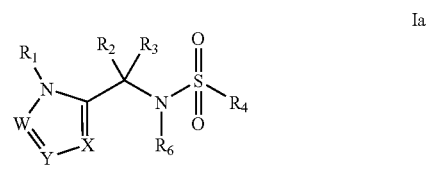

Ia

In formula Ia, the symbols $R_1$, $R_2$, $R_3$, $R_4$, $R_6$, W, X, and Y have the following meanings.

$R_1$ is selected from the group consisting of lower alkyl, substituted lower alkyl, phenyl, substituted phenyl, benzyl, substituted benzyl, benzyloxy, substituted benzyloxy, and $SO_2R_5$;

$R_5$ is selected from phenyl, substituted phenyl, heterocycle, substituted heterocycle, alkyl, and substituted alkyl.

$R_2$ is selected from lower alkyl, substituted lower alkyl, $CF_3$, alkenyl, substituted alkenyl, alkynyl, substituted alkynyl, phenyl, substituted phenyl, and cycloalkyl.

$R_3$ is selected from hydrogen, lower alkyl, or substituted lower alkyl.

$R_4$ is selected from phenyl, substituted phenyl, heterocycle, substituted heterocycle, thiophene, and substituted thiophene.

$R_6$ is selected from hydrogen, lower alkyl, substituted lower alkyl, $CF_3$, alkenyl, substituted alkenyl, alkynyl, substituted alkynyl, phenyl, substituted phenyl, cycloalkyl, and substituted cycloalkyl.

W, X and Y are independently selected from $CR_7$ or N.

$R_7$ is selected from hydrogen, halogen, lower alkyl, and substituted lower alkyl.

Of these compounds, the preferred members are those in which $R_1$ is (substituted) benzyl or (substituted) phenyl; $R_2$ is lower alkyl, $R_3$ is hydrogen, $R_4$ is 5-chloro-2-thiophene, W=N, X=CH or N, Y=CH, and $R_6$ is H.

The present invention also provides compounds of the formula Ia and pharmaceutically acceptable salts and/or hydrates or prodrugs thereof, wherein:

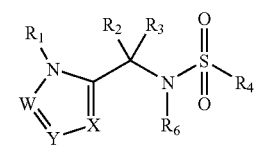

In this formula, the symbols $R_1$, $R_2$, $R_3$, $R_4$, $R_6$, W, X, and Y have the following meanings.

$R_1$ is selected from the group consisting of lower alkyl, substituted lower alkyl, phenyl, substituted phenyl, benzyl, substituted benzyl, benzyloxy, substituted benzyloxy, and $SO_2R_5$;

$R_5$ is selected from phenyl, substituted phenyl, heterocycle, substituted heterocycle, alkyl, and substituted alkyl.

$R_2$ is selected from lower alkyl, substituted lower alkyl, $CF_3$, alkenyl, substituted alkenyl, alkynyl, substituted alkynyl, phenyl, substituted phenyl, and cycloalkyl.

$R_3$ is selected from hydrogen, lower alkyl, or substituted lower alkyl.

$R_4$ is selected from phenyl, substituted phenyl, heterocycle, substituted heterocycle, thiophene, and substituted thiophene.

$R_6$ is hydrogen.

W, X and Y are independently selected from $CR_7$ or N.

$R_7$ is selected from hydrogen, halogen, lower alkyl, and substituted lower alkyl.

Preferred compounds prepared according to the present invention include 5-Chloro-N-{2-ethyl-1-[1-(4-methoxybenzyl)-1H-pyrazol-5-yl]butyl}thiophene-2-sulfonamide; 4-Chloro-N-{2-ethyl-1-[1-(4-methoxybenzyl)-1H-pyrazol-5-yl]butyl}benzenesulfonamide; 4-Bromo-N-{2-ethyl-1-[1-(4-methoxybenzyl)-1H-pyrazol-5-yl]butyl}benzenesulfonamide; 5-Chloro-N-{1-[1-(4-methoxybenzyl)-1H-pyrazol-5-yl]ethyl}thiophene-2-sulfonamide; 5-Chloro-N-{1-[1-(4-methoxybenzyl)-1H-pyrazol-5-yl]-2-methylpropyl}thiophene-2-sulfonamide; 5-Chloro-N-{1-[1-(4-methoxybenzyl)-1H-pyrazol-5-yl]butyl}thiophene-2-sulfonamide; N-[1-(1-Butyl-1H-pyrazol-5-yl)-2-ethylbutyl]-5-chlorothiophene-2-sulfonamide; 5-Chloro-N-{2-ethyl-1-[1-(4-hydroxybenzyl)-1H-pyrazol-5-yl]butyl}thiophene-2-sulfonamide; 5-Chloro-N-(2-ethyl-1-{1-[(4-methylphenyl)sulfonyl]-1H-pyrazol-5-yl}butyl)thiophene-2-sulfonamide; 5-Chloro-N-{2-ethyl-1-[1-(4-methoxyphenyl)-1H-pyrazol-5-yl]butyl}thiophene-2-sulfonamide; 5-Chloro-N-{2-ethyl-1-[1-(4-hydroxyphenyl)-1H-pyrazol-5-yl]butyl}thiophene-2-sulfonamide; 5-Chloro-N-[2-methyl-1-(1-phenyl-1H-pyrazol-5-yl)propyl]thiophene-2-sulfonamide; 5-Chloro-N-[1-(1-phenyl-1H-pyrazol-5-yl)ethyl]thiophene-2-sulfonamide; 5-Chloro-N-{2-methyl-1-[1-(4-methylphenyl)-1H-pyrazol-5-yl]propyl}thiophene-2-sulfonamide; 5-Chloro-N-{1-[1-(4-fluorophenyl)-1H-pyrazol-5-yl]-2-methylpropyl}thiophene-2-sulfonamide; 5-Chloro-N-{2-methyl-1-[1-(3-methylphenyl)-1H-pyrazol-5-yl]propyl}thiophene-2-sulfonamide; 5-Chloro-N-[2-ethyl-1-(1-phenyl-1H-pyrazol-5-yl)butyl]thiophene-2-sulfonamide; 5-Chloro-N-(2-ethyl-1-{1-[4-(trifluoromethyl)phenyl]-1H-pyrazol-5-yl} butyl)thiophene-2-sulfonamide; 5-Chloro-N-{2-ethyl-1-[1-(4-fluorobenzyl)-1H-1,2,4-triazol-5-yl]butyl}thiophene-2-sulfonamide; 5-Chloro-N-(2-ethyl-1-{1-[4-(trifluoromethoxy)benzyl]-1H-1,2,4-triazol-5-yl}butyl)thiophene-2-sulfonamide; 5-Chloro-N-{2-ethyl-1-[1-(4-methoxybenzyl)-1H-1,2,4-triazol-5-yl]butyl}thiophene-2-sulfonamide; N-[1-(1-Benzyl-1H-1,2,4-triazol-5-yl)-2-ethylbutyl]-5-chlorothiophene-2-sulfonamide; N-[1-(1-Benzyl-1H-1,2,4-triazol-5-yl)-2-methylpropyl]-5-chlorothiophene-2-sulfonamide; 5-Chloro-N-{2-methyl-1-[1-(4-methylbenzyl)-1H-1,2,4-triazol-5-yl]propyl}thiophene-2-sulfonamide; N-[1-(1-Benzyl-1H-1,2,4-triazol-5-yl)ethyl]-5-chlorothiophene-2-sulfonamide; 5-Chloro-N-{1-[1-(4-methylbenzyl)-1H-1,2,4-triazol-5-yl]ethyl}thiophene-2-sulfonamide; 5-Chloro-N-{2-ethyl-1-[1-(4-methylbenzyl)-1H-1,2,4-triazol-5-yl]butyl}thiophene-2-sulfonamide; N-[1-(1-Benzyl-1H-imidazol-2-yl)-2-ethylbutyl]-5-chlorothiophene-2-sulfonamide; 5-Chloro-N-{2-ethyl-1-[1-(4-methoxybenzyl)-1H-imidazol-2-yl]butyl}thiophene-2-sulfonamide; 5-Chloro-N-{2-ethyl-1-[1-(4-hydroxybenzyl)-1H-imidazol-2-yl]butyl}thiophene-2-sulfonamide; N-[1-(1-Benzyl-1H-pyrrol-2-yl)-2-methylpropyl]-5-chlorothiophene-2-sulfonamide; 5-Chloro-N-{1-[1-(4-methoxybenzyl)-1H-pyrrol-2-yl]-2-methylpropyl}thiophene-2-sulfonamide; N-{1-[1-(Benzyloxy)-1H-pyrazol-5-yl]-2-ethylbutyl}-5-chlorothiophene-2-sulfonamide; 5-Chloro-N-{(4-fluorophenyl)[1-(4-fluorophenyl)-1H-pyrazol-5-yl]methyl}thiophene-2-sulfonamide; 5-Chloro-N-{1-[1-(4-fluorophenyl)-1H-pyrazol-5-yl]-2-phenylethyl}thiophene-2-sulfonamide; 4-Chloro-N-[2-ethyl-1-(1-phenyl-1H-pyrazol-5-yl)butyl]benzenesulfonamide; 4-Cyano-N-[2-ethyl-1-(1-phenyl-1H-pyrazol-5-yl)butyl]benzenesulfonamide; 4,5-Dichloro-N-[2-ethyl-1-(1-phenyl-1H-pyrazol-5-yl)butyl]thiophene-2-sulfonamide; 3,4-Dichloro-N-[2-ethyl-1-(1-phenyl-1H-pyrazol-5-yl)butyl]benzenesulfonamide; 5-Bromo-N-[2-ethyl-1-(1-phenyl-1H-pyrazol-5-yl)butyl]thiophene-2-sulfonamide; 5-Chloro-N-{(1R)-1-[1-(4-fluorophenyl)-1H-pyrazol-5-yl]-2-methylpropyl}thiophene-2-sulfonamide; 5-Chloro-N-{(1S)-1-[1-(4-fluorophenyl)-1H-pyrazol-5-yl]-2-methylpropyl}thiophene-2-sulfonamide; 4-Cyano-N-[2-ethyl-1-(1-phenyl-1H-pyrazol-5-yl)butyl]-N-methylbenzenesulfonamide; 4-Chloro-N-[2-ethyl-1-(1-phenyl-1H-pyrazol-5-yl)butyl]-N-methylbenzenesulfonamide; 4,5-Dichloro-N-[2-ethyl-1-(1-phenyl-1H-pyrazol-5-yl)butyl]-N-methylthiophene-2-sulfonamide; 5-Chloro-N-[2-ethyl-1-(1-phenyl-1H-pyrazol-5-yl)butyl]-N-methylthiophene-2-sulfonamide; 3,4-Dichloro-N-[2-ethyl-1-(1-phenyl-1H-pyrazol-5-yl)butyl]-N-methylbenzenesulfonamide; and 5-Bromo-N-[2-ethyl-1-(1-phenyl-1H-pyrazol-5-yl)butyl]-N-methylthiophene-2-sulfonamide, or a pharmaceutically acceptable salt thereof.

The compounds of the invention may contain one or more asymmetric carbon atoms and some of the compounds may contain one or more asymmetric (chiral) centers and may thus give rise to optical isomers and diastereomers. Thus, the invention includes such optical isomers and disastereomers; as well as the racemic and resolved, enantiomerically pure stereoisomers; as well as other mixtures of the R and S stereoisomers, and pharmaceutically acceptable salts, hydrates, and prodrugs thereof.

The term "alkyl" is used herein as a group or part of a group refers to both straight- and branched-chain saturated aliphatic hydrocarbon groups having one to ten carbon atoms, preferably one to eight carbon atoms and, most preferably, one to six carbon atoms; as used herein, the term "lower alkyl" refers to straight- and branched-chain saturated aliphatic hydrocarbon groups having one to six carbon atoms; "alkenyl" is intended to include both straight- and branched-chain alkyl group with at least one carbon-carbon double bond and two to eight carbon atoms, preferably two to six carbon atoms; "alkynyl" group is intended to cover both straight- and branched-chain alkyl groups with at least one carbon-carbon triple bond and two to eight carbon atoms, preferably two to six carbon atoms.

The terms "substituted alkyl", "substituted lower alkyl", "substituted alkenyl", and "substituted alkynyl" refer to alkyl, alkenyl, and alkynyl as just described having from one to three substituents selected from the group including halogen, CN, OH, $NO_2$, amino, aryl, heterocyclic, substituted aryl, substituted heterocyclic, alkoxy, substituted alkoxy, aryloxy, substituted alkyloxy, alkylcarbonyl, alkylcarboxy, alkylamino, and arylthio. These substituents may be attached to any carbon of an alkyl, alkenyl, or alkynyl group provided that the attachment constitutes a stable chemical moiety.

The term "aryl" is used herein as a group or part of a group refers to a carbocyclic aromatic system, which may be a single ring, or multiple aromatic rings fused or linked together as such that at least one part of the fused or linked rings forms the conjugated aromatic system and may for example comprise 6 to 14 carbon atoms. The aryl groups include, but are not limited to, phenyl, naphthyl, biphenyl, anthryl, tetrahydronaphthyl, phenanthryl, and indane.

The term "substituted aryl" refers to aryl as just defined having one to four substituents from the group including halogen, CN, OH, $NO_2$, amino, alkyl, cycloalkyl, alkenyl, alkynyl, alkoxy, aryloxy, substituted alkyloxy, alkylcarbonyl, alkylcarboxy, alkylamino, and arylthio.

The term "substituted benzyl" refers to a benzyl group, having substituted on the benzene ring, one to five substituents from the group including halogen, $CF_3$, $CF_3O$—, CN, OH, $NO_2$, amino, alkyl, cycloalkyl, alkenyl, alkynyl, alkoxy, aryloxy, substituted alkyloxy, alkylcarbonyl, alkylcarboxy, alkylamino, and arylthio.

The terms "heterocyclic ring" or "heterocycle" are used herein to describe a stable 4- to 7-membered monocyclic or a stable multicyclic heterocyclic ring which is saturated, partially unsaturated, or unsaturated, and which consists of carbon atoms and from one to four heteroatoms selected from the group including N, O, and S atoms. The N and S atoms may be oxidized. The heterocyclic ring also includes any multicyclic ring in which any of above defined heterocyclic rings is fused to an aryl (e.g. benzene) ring. The heterocyclic ring may be attached at any heteroatom or carbon atom provided the resultant structure is chemically stable. Such heterocyclic groups include, for example, tetrahydrofuran, piperidinyl, piperazinyl, 2-oxopiperidinyl, azepinyl, pyrrolidinyl, imidazolyl, pyridyl, pyrazinyl, pyrimidinyl, pyridazinyl, oxazolyl, isoxazolyl, morpholinyl, indolyl, quinolinyl, thienyl, furyl, benzofuranyl, benzothienyl, thiamorpholinyl, thiamorpholinyl sulfoxide, isoquinolinyl, and tetrahydrothiopyran.

The term "substituted heterocycle" is used herein to describe the heterocyclic just defined having one to four substituents selected from the group which includes halogen, CN, OH, $NO_2$, amino, alkyl, substituted alkyl, cycloalkyl, substituted cycloalkyl, alkenyl, substituted alkenyl, alkynyl, substituted alkynyl, alkoxy, substituted alkoxy, aryloxy, substituted aryloxy, alkyloxy, substituted alkyloxy, alkylcarbonyl, substituted alkylcarbonyl, alkylcarboxy, substituted alkylcarboxy, alkylamino, substituted alkylamino, arylthio, or substituted arylthio.

The term "cycloalkyl" is used herein to describe a carbon-based ring having more than 3 carbon-atoms, e.g. up to 8 carbon atoms, which forms a stable ring. The term "substituted cycloalkyl" refers to cycloalkyl rings having from one to five substituents selected from the group consisting of halogen, CN, OH, $NO_2$, amino, alkyl, substituted alkyl, alkenyl, substituted alkenyl, alkynyl, alkoxy, aryloxy, substituted alkyloxy, alkylcarbonyl, alkylcarboxy, alkylamino, substituted alkylamino, arylthio, heterocyclic, substituted heterocyclic, aminoalkyl, and substituted aminoalkyl.

Where the terms "substituted alkyl" or "substituted alkylphenyl" are recited, the substitution may occur at the alkyl group or on the corresponding base compound.

The term "alkoxy" is used herein to refer to the OR group, where R is alkyl or substituted alkyl. The term "aryloxy" is used herein to refer to the OR group, where R is aryl or substituted aryl. The term "alkylcarbonyl" is used herein to refer to the RCO group, where R is alkyl or substituted alkyl. The term "alkylcarboxy" is used herein to refer to the COOR group, where R is alkyl or substituted alkyl. The term "aminoalkyl" refers to both secondary and tertiary amines wherein the alkyl or substituted alkyl groups, containing one to eight carbon atoms, which may be either same or different and the point of attachment is on the nitrogen atom. The term "alkylamino" refers to the $RNH_2$ group, where R is alkyl or substituted alkyl.

Where "aminoalkyl", "alkylamino", "alkylcarboxy", "alkoxy" or "alkylcarbonyl" groups are substituted, the substituents are the same as those for "alkyl" as defined above.

The term "halogen" refers to Cl, Br, F, or I.

The term "ring" structure, includes a monocyclic structure, a bridged cyclo structure, and fused cyclo structures, unless the type of ring structure is otherwise specified.

The compounds of the present invention can be used in the form of salts derived from pharmaceutically or physiologically acceptable acids or bases. These salts include, but are not limited to, the following salts with organic and inorganic acids such as acetic, lactic, citric, tartaric, succinic, fumaric, maleic, malonic, mandelic, mallic, hydrochloric, hydrobromic, phosphoric, nitric, sulfuric, methanesulfonic, toluenesulfonic and similarly known acceptable acids, and mixtures thereof. Other salts include diethanolamine, ethylenediamine, and salts with alkali metals or alkaline earth metals, such as sodium (e.g., sodium hydroxide), potassium (e.g., potassium hydroxide), calcium (e.g., calcium hydroxide) or magnesium (e.g., magnesium hydroxide).

These salts, as well as other compounds of the invention may be in the form of esters, carbamates and other conventional "pro-drug" forms, which, when administered in such form, convert to the active moiety in vivo. In a currently preferred embodiment, the prodrugs are esters. See, e.g., 3. Testa and J. Caldwell, "Prodrugs Revisited: The "Ad Hoc" Approach as a Complement to Ligand Design", Medicinal Research Reviews, 16(3):233-241, ed., John Wiley & Sons (1996).

Methods of Use

Compounds of Formula (Ia) are inhibitors of beta amyloid production. In preliminary studies using protease specific assays, exemplary compounds of Formula (Ia) have been shown to exhibit specific inhibition with respect to protease activity. Thus, the compounds of the present invention are useful for treatment and prevention of a variety of conditions in which modulation of beta amyloid levels provides a therapeutic benefit. Such conditions include, e.g., amyloid angiopathy, cerebral amyloid angiopathy, systemic amyloidosis, Alzheimer's Disease (AD), hereditary cerebral hemorrhage with amyloidosis of the Dutch type, inclusion body myositis, Down's syndrome, mild cognitive impairment (MCI), among others.

In addition, the compounds of Formula (Ia) may be utilized in generating reagents useful in diagnosis of conditions associated with abnormal levels of beta amyloid. For example, the compounds of Formula (Ia) may be used to generate antibodies, which would be useful in a variety of diagnostic assays. Methods for generating monoclonal, polyclonal, recombinant, and synthetic antibodies or fragments thereof, are well known to those of skill in the art. (See, e.g., E. Mark and Padlin, "Humanization of Monoclonal Antibodies", Chapter 4, *The Handbook of Experimental Pharmacology*, Vol. 113, The Pharmacology of Monoclonal Antibodies, Springer-Verlag (June, 1994); Kohler and Milstein and the many known modifications thereof; International Patent Application No. PCT/GB85/00392; British Patent Application Publication No. GB2188638A; Amit et al., *Science*, 233:747-753 (1986); Queen et al., *Proc. Nat'l. Acad. Sci. USA*, 86:10029-10033 (1989); International Patent Publication No. WO90/07861; and Riechmann et al., *Nature*, 332:323-327 (1988); Huse et al, *Science*, 246:1275-1281 (1988)). Alternatively, the compounds of Formula (Ia) may themselves be used in such diagnostic assays. Regardless of the reagent selected (e.g., antibody or compound of Formula (Ia)), suitable diagnostic formats including, e.g., radioimmunoassays and enzyme-linked immunosorbent assays (ELISAs), are well known to those of skill in the art and are not a limitation on this embodiment of the invention.

The beta amyloid inhibitory activity of many of the compounds of the present invention has been determined using the Repressor Release Assay (RRA). See, Table 3 below. A compound is considered active in RRA if it leads to at least a 1.5 fold increase in luciferase activity at 20 μg/mL and is non-toxic.

Additionally, cellular, cell-free and in vivo screening methods to detect inhibitors of beta amyloid production are known in the art. Such assays may include radioimmunoassays and enzyme-linked immunosorbent assay (ELISA), among others. See, e.g., P. D. Mehta, et al., Techniques in Diagnostic Pathology, vol. 2, eds., Bullock et al, Academic Press, Boston, pages 99-112 (1991), International Patent Publication No. WO 98/22493, European Patent No. 0652009, U.S. Pat. No. 5,703,129 and U.S. Pat. No. 5,593,846. Selection of an appropriate in vitro or in vivo screening assay is not a limitation of the present invention.

These and the other compounds of the invention can be prepared following the Schemes illustrated below.

Synthesis

The compounds of the present invention can be prepared in a number of ways well known to one skilled in the art of organic synthesis. The compounds of the present invention can be prepared using the methods described in Schemes 1 and 2, together with synthetic methods known in the synthetic organic arts or variations of these methods by one skilled in the art. (See, generally, *Comprehensive Organic Synthesis*, "Selectivity, Strategy & Efficiency in Modern Organic Chemistry", ed., I. Fleming, Pergamon Press, New York (1991); *Comprehensive Organic Chemistry*, "The Synthesis and Reactions of Organic Compounds", ed. J. F. Stoddard, Pergamon Press, New York (1979)). Preferred methods include, but are not limited to, those outlined below.

A first method of preparation consists of reacting pyrazole I (W=N, Y=CH, X=CH, Z=H) or imidazole I (W=CH, Y=CH, X=N, Z=H) with a suitable base such as NaH or $K_2CO_3$ and $R_1Q$ ($R_1$=benzyl, substituted benzyl, $SO_2R_5$, or lower alkyl; Q=Br or Cl) in a suitable solvent to afford substituted pyrazole II (W=N, Y=CH, X=CH, $R_1$=benzyl, substituted benzyl, $SO_2R_5$, or lower alkyl) or imidazole II (W=CH, Y=CH, X=N, $R_1$=benzyl, substituted benzyl, $SO_2R_5$, or lower alkyl), respectively. Alternatively, benzyloxypyrazoles II (W=N, Y=CH, X=CH, $R_1$=benzyloxy or substituted benzyloxy) can be prepared by reacting pyrazol-1-ol I (W=N, Y=CH, X=CH, Z=OH) with a suitable base such as diisopropylethylamine and (substituted) benzyl bromide. Alternatively, substituted phenyl pyrazoles II ($R_1$=phenyl, substituted phenyl, W=N, Y=CH, X=CH) can be prepared by treatment of I (W=N, Y=CH, X=CH, Z=H) with a (substituted) phenyl boronic acid, pyridine, and cupric acetate. Alternatively, substituted 1,2,4-triazoles II (W=N, Y=CH, X=N, $R_1$=benzyl, substituted benzyl, $SO_2R_5$, or lower alkyl) can be prepared by treatment of 1,2,4-triazole I (W=N, Y=CH, X=N, Z=H) with $R_1Q$ ($R_1$=benzyl, substituted benzyl, $SO_2R_5$, lower alkyl; Q=Br, Cl) and DBU.

N-Substituted heterocycles II can be lithiated by treatment with n-BuLi or t-BuLi and then reacted with an aldehyde ($R_3$=H) or ketone to provide alcohol III. Alternatively, pyrroles III (W=CH, Y=CH, X=CH, $R_3$=H) can be prepared by reacting N-substituted pyrrol-2-aldehydes VII with a suitable Grignard reagent. Azides IV can be obtained by treatment of alcohols III with DPPA, DEAD, and $Ph_3P$ or by utilizing a two step procedure by first treating alcohol III with methanesulfonyl chloride and triethylamine and then reacting the resulting mesylate with sodium azide. Azide IV can be converted to amine V by utilizing standard methodology such as hydrogenation with Pd/C or triphenylphosphine and water. Reaction of amine V with a suitable sulfonyl halide in the presence of a base such as triethylamine in a suitable solvent affords compounds of formula VI ($R_6$=H). Treatment of VI ($R_6$=H) with a suitable base such as NaH and $R_6Q$ ($R_6$=alkyl, Q=Br, Cl, I) affords VI ($R_6$=alkyl).

Scheme I

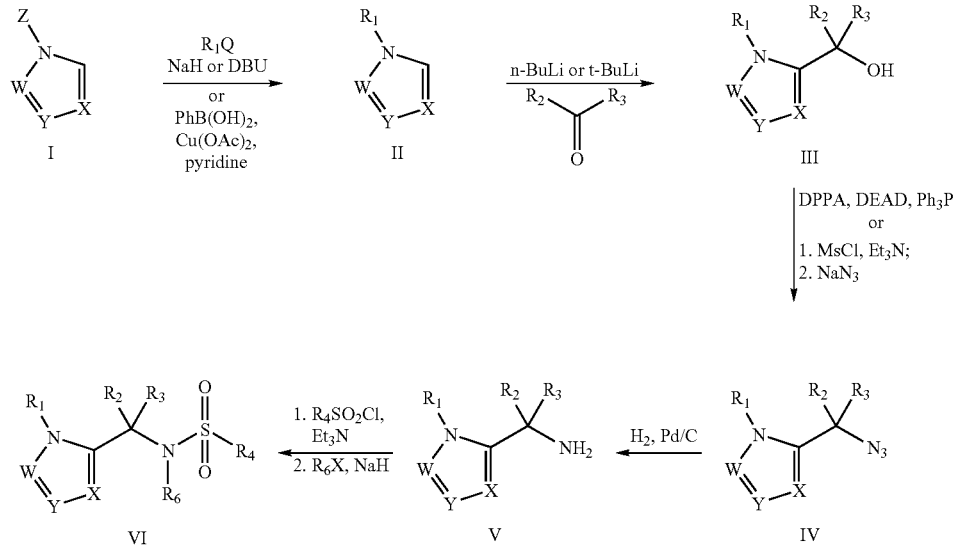

Scheme II

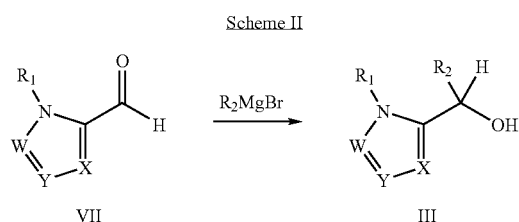

As has been mentioned previously, elevated beta amyloid levels in brain correlate with cognitive decline. The compounds of the present invention have utility for the prevention and treatment of disorders involving beta amyloid production including cerebrovascular diseases. The compounds of the present invention have utility for the prevention and treatment of AD by virtue of their ability to reduce beta amyloid production.

Cellular, cell-free and in vivo screening methods to detect inhibitors of beta amyloid production are known in the art (for example International Patent Publication No. WO98/22493, European Patent No. 0652009, and U.S. Pat. Nos. 5,703,129 and 5,593,846). In one embodiment, inhibition of beta amyloid production is determined by the cellular Repressor Release Assay (RRA) described below.

Pharmaceutical Formulation

The compounds of this invention may be administered to a subject by any desirable route, taking into consideration the specific condition for which it has been selected. By subject is meant any suitable mammal, including humans, domestic animals (e.g., canines and felines), and livestock, which have been recognized as having or at risk of having one or more of the conditions for which modulation of beta amyloid levels is desirable. Thus, the compounds of the invention are useful for treatment and/or prevention of a number of human and veterinary conditions. As used herein, "prevention" encompasses prevention of symptoms in a subject who has been identified as at risk for the condition, but has not yet been diagnosed with the same and/or who has not yet presented any symptoms thereof.

These compounds may be delivered or administered by any suitable route of delivery, e.g., oral, injection, inhalation (including oral, intranasal and intratracheal), intravenous, subcutaneous, intramuscular, sublingual, intracranial, epidural, intratracheal, rectal, vaginal, among others. Most desirably, the compounds are delivered orally, by inhalation or by a suitable parenteral route. The compounds may be formulated in combination with conventional pharmaceutical carriers that are physiologically compatible. Optionally, one or more of the compounds of the invention may be mixed with other active agents.

Suitable physiologically compatible carriers may be readily selected by one of skill in the art. For example, suitable solid carriers include, among others, one or more substances which may also act as flavoring agents, lubricants, solubilizers, suspending agents, fillers, glidants, compression aids, binders or tablet-disintegrating agents or an encapsulating material. In powders, the carrier is a finely divided solid, which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium or dicalcium phosphate, magnesium stearate, talc, starch, sugars (including, e.g., lactose and sucrose), cellulose (including, e.g., microcrystalline cellulose, methyl cellulose, sodium caroboxymethyl cellulose), polyvinylpyrrolidine, low melting waxes, ion exchange resins, and kaolin.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, suspending agents, thickening agents, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols, e.g., glycols) and their derivatives, and oils (e.g., fractionated coconut oil, arachis oil, corn oil, peanut oil, and sesame oil). For parenteral administration the carrier can also be an oily ester such as ethyl oleate and isopropyl myristate. Sterile liquid carriers are used in sterile liquid form compositions for parenteral administration.

Optionally, additives customarily employed in the preparation of pharmaceutical compositions may be included in the compositions of the invention. Such components include, e.g., sweeteners or other flavoring agents, coloring agents, preservatives, and antioxidants, e.g., vitamin E, ascorbic acid, BHT and BHA.

Liquid pharmaceutical compositions that are sterile solutions or suspensions can be utilized by, for example, intramuscular, intraperitoneal or subcutaneous injection. Sterile solutions can also be administered intravenously. Oral administration may be either liquid or solid composition form.

Suitably, when prepared for use as an inhalant, the pharmaceutical compositions are prepared as fluid unit doses using a compound of the invention and a suitable pharmaceutical vehicle for delivery by an atomizing spray pump, or by dry powder for insufflation. For use as aerosols, the compound of the invention is formulated for and packaged in a pressurized aerosol container together with a gaseous or liquefied propellant, for example, dichlorodifluoromethane, carbon dioxide, nitrogen, propane, and the like, with the usual components such as cosolvents and wetting agents, as may be necessary or desirable. For example, the invention provides for delivery of a metered dose for oral or intranasal inhalation in one, two, or more actuations. Suitably, a dose is delivered in one or two actuations. However, other suitable delivery methods may be readily determined.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

As described herein, a therapeutically or prophylactically useful amount of a compound of the invention is that amount of a compound which alleviates the symptoms of the disease, e.g., AD, or which prevents the onset of symptoms, or the onset of more severe symptoms. The useful amounts of a compound may vary depending upon the formulation and route of delivery. For example, higher amounts may be delivered orally than when the compound is formulated for injection or inhalation, in order to deliver a biologically equivalent amount of the drug. Suitably, an individual dose (i.e., per unit) of a compound of the invention is in the range from about 1 µg/kg to about 10 g/kg. However, in certain embodiments, these doses may be selected from a lower range, e.g., from about 1 µg/kg to about 200 mg/kg, more preferably 10 µg/kg to about 10 mg/kg, and most preferably about 100 µg/kg to about 1 mg/kg. Desirably, these amounts are provided on a daily basis. However, the dosage to be used in the treatment or prevention of a specific cognitive deficit or other condition may be subjectively determined by the attending physician. The variables involved include the specific cognitive deficit and the size, age and response pattern of the patient. For example, based upon the activity profile and potency of the compounds of this invention, a starting dose of about 375 to 500 mg per day with gradual increase in the daily dose to about 1000 mg per day may provide the desired dosage level in the human.

Alternatively, the use of sustained delivery devices may be desirable, in order to avoid the necessity for the patient to take medications on a daily basis. "Sustained delivery" is defined as delaying the release of an active agent, i.e., a compound of the invention, until after placement in a delivery environment, followed by a sustained release of the agent at a later time. Those of skill in the art know suitable sustained delivery devices. Examples of suitable sustained delivery devices include, e.g., hydrogels (U.S. Pat. Nos. 5,266,325; 4,959,217; and 5,292,515), an osmotic pump, such as described by Alza (U.S. Pat. Nos. 4,295,987 and 5,273,752) or Merck (European Patent No. 314,206), among others; hydrophobic membrane materials, such as ethylenemethacrylate (EMA) and ethylenevinylacetate (EVA); bioresorbable polymer systems (see, e.g., International Patent Publication No. WO 98/44964, Bioxid and Cellomeda; U.S. Pat. No. 5,756,127 and U.S. Pat. No. 5,854,388); other bioresorbable implant devices have been described as being composed of, for example, polyesters, polyanhydrides, or lactic acid/glycolic acid copolymers (see, e.g., U.S. Pat. No. 5,817,343 (Alkermes Inc.)). For use in such sustained delivery devices, the compounds of the invention may be formulated as described herein.

In another aspect, the invention provides a pharmaceutical kit for delivery of a product. Suitably, the kit contains packaging or a container with the compound formulated for the desired delivery route. For example, if the kit is designed for administration by inhalation, it may contain a suspension containing a compound of the invention formulated for aerosol or spray delivery of a predetermined dose by inhalation. Suitably, the kit contains instructions on dosing and an insert regarding the active agent. Optionally, the kit may further contain instructions for monitoring circulating levels of product and materials for performing such assays including, e.g., reagents, well plates, containers, markers or labels, and the like. Such kits are readily packaged in a manner suitable for treatment of a desired indication. For example, the kit may also contain instructions for use of the spray pump or other delivery device.

Other suitable components to such kits will be readily apparent to one of skill in the art, taking into consideration the desired indication and the delivery route. The doses may be repeated daily, weekly, or monthly, for a predetermined length of time or as prescribed.

The following examples are illustrative of compounds of formula Ia of the invention, and methods of synthesizing same. It will be readily understood by one of skill in the art that the specific conditions described herein for producing these compounds can be varied without departing from the scope of the present invention. It will be further understood that other compounds of formula Ia, as well as other salts, hydrates, and/or prodrugs thereof, are within the scope of the invention.

EXAMPLE 1

5-Chloro-N-{2-ethyl-1-[1-(4-methoxybenzyl)-1H-pyrazol-5-yl]butyl}thiophene-2-sulfonamide A. 2-Ethyl-1-[1-(4-methoxybenzyl)-1H-pyrazol-5-yl]butan-1-ol To 1-(4-methoxybenzyl)-1H-pyrazole (*Synthetic Comm.* 25(5), 761-774 (1995)) (2.43 g, 12.9 mmol) in THF (100 mL) at −78° C. was added a solution of n-BuLi (2 M in cyclohexane, 7.1 mL, 14.2 mmol) dropwise. After 75 min, 2-ethylbutyraldehyde (1.3 mL, 10.6 mmol) was added. After 45 min the reaction mixture was quenched with saturated aqueous ammonium chloride (50 mL), extracted with EtOAc (3×100 mL), dried ($Na_2SO_4$) and concentrated. Column chromatography (EtOAc/hexanes, 1:4) provided 1.37 g (37%) of 2-ethyl-1-[1-(4-methoxybenzyl)-1H-pyrazol-5-yl]butan-1-ol as an oil.

$^1$H NMR (400 MHz, DMSO-$d_6$): δ 0.66 (t, 3H, J=7.4 Hz), 0.73 (t, 3H, J=7.4 Hz), 1.01-1.12 (m, 2H), 1.29-1.50 (m, 3H), 3.70 (s, 3H), 4.51 (t, 1H, J=6.5 Hz), 5.21 (d, 1H, J=5.7 Hz), 5.26 (d, 2H, J=3.5 Hz), 6.15 (d, 1H, J=1.5 Hz), 6.85 (d, 2H, J=8.6 Hz), 7.06 (d, 2H, J=8.6 Hz), 7.36 (d, 1H, J=1.5 Hz);
Mass Spectrum (+ESI): 289 (M+H)$^+$.

B. 5-(1-Azido-2-ethylbutyl)-1-(4-methoxybenzyl)-1H-pyrazole

To 2-ethyl-1-[1-(4-methoxybenzyl)-1H-pyrazol-5-yl]butan-1-ol (1.21 g, 4.20 mmol) in THF (40 mL) at 0° C. was added triphenylphosphine (1.65 g, 6.29 mmol), diethyl azodicarboxylate (1.0 mL, 6.3 mmol), and diphenylphosphoryl azide (1.4 mL, 6.3 mmol). The reaction mixture was warmed to room temperature and stirred for 15.5 h. The solvent was removed in vacuo and the resulting residue was purified by column chromatography (EtOAc/hexanes, 1:9, then 1:4) to give 0.862 g (66%) of 5-(1-azido-2-ethylbutyl)-1-(4-methoxybenzyl)-1H-pyrazole.

$^1$H NMR (400 MHz, DMSO-$d_6$): δ 0.66 (t, 3H, J=7.5 Hz), 0.76 (t, 3H, J=7.4 Hz), 0.99-1.07 (m, 2H), 1.32-1.39 (m, 1H), 1.46-1.52 (m, 1H). 1.56-1.62 (m, 1H), 3.70 (s, 3H), 4.69 (d, 1H, J=8.9 Hz), 5.34 (s, 2H), 6.36 (d, 1H, J=1.8 Hz), 6.87 (d, 2H, J=8.6 Hz), 7.08 (d, 2H, J=8.6 Hz), 7.51 (d, 1H, J=1.8 Hz);
Mass Spectrum (+ESI): 314 (M+H)$^+$.

C. {2-Ethyl-1-[1-(4-methoxybenzyl)-1H-pyrazol-5-yl]butyl}amine 5-(1-Azido-2-ethylbutyl)-1-(4-methoxybenzyl)-1H-pyrazole (0.750 g, 2.39 mmol) in MeOH (24 mL) with 5% Pd/C (75 mg) was hydrogenated under atm pressure for 24 h. The reaction mixture was filtered through a plug of Celite and the filtrate was concentrated to give 0.637 g (93%) of {2-ethyl-1-[1-(4-methoxybenzyl)-1H-pyrazol-5-yl]butyl}amine as an oil.

$^1$H NMR (400 MHz, DMSO-$d_6$): δ 0.67-0.72 (m, 6H), 1.05-1.27 (m, 3H), 1.37-1.44 (m, 1H), 1.60 (br s, 2H), 3.70 (s, 3H), 3.82 (d, 1H, J=5.5 Hz), 5.25 (q, 2H, J=15.7 Hz), 6.18 (d, 1H, J=1.5 Hz), 6.86 (d, 2H, J=8.7 Hz), 7.03 (d, 2H, J=8.7 Hz), 7.35 (d, 1H, J=1.5 Hz); Mass Spectrum (+ESI): 288 (M+H)$^+$.

D. 5-Chloro-N-{2-ethyl-1-[1-(4-methoxybenzyl)-1H-pyrazol-5-yl]butyl}thiophene-2-sulfonamide To {2-ethyl-1-[1-(4-methoxybenzyl)-1H-pyrazol-5-yl]butyl}amine (0.500 g, 1.74 mmol) in $CH_2Cl_2$ (15 mL) was added triethylamine (0.29 mL, 2.1 mmol) and 5-chlorothiophene-2-sulfonyl chloride (0.450 g, 2.09 mmol). After 2 days the reaction mixture was diluted with EtOAc (30 mL), washed with 1 N HCl (30 mL), dried ($Na_2SO_4$) and concentrated. Column chromatography (EtOAc/hexane, 3:7, then 1:1) provided 5-chloro-N-{2-ethyl-1-[1-(4-methoxybenzyl)-1H-pyrazol-5-yl]butyl}thiophene-2-sulfonamide (0.415 g, 51%) as an oil.

$^1$H NMR (400 MHz, DMSO-$d_6$): δ 0.62 (t, 3H, J=7.4 Hz), 0.70 (t, 3H J=7.3 Hz), 0.93-1.04 (m, 2H), 1.16-1.40 (m, 3H), 3.71 (s, 3H), 4.46 (m, 1H), 5.20 (q, 2H, J=15.8 Hz), 6.12 (d, 1H, J=1.8 Hz), 6.84 (d, 1H, J=4.1 Hz), 6.88 (d, 2H, J=8.7 Hz), 6.95 (d, 1H, J=4.0 Hz), 7.05 (d, 2H, J=8.7 Hz), 7.24 (d, 1H, J=1.8 Hz), 8.46 (d, 1H, J=9.5 Hz); Mass Spectrum (−ESI): 466 (M−H)$^-$.

Anal: Calc'd for $C_{21}H_{26}ClN_3O_3S_2$ C, 53.89; H, 5.60; N, 8.98. Found: C, 53.96; H, 5.72; N, 8.66.

EXAMPLE 2

4-Chloro-N-{2-ethyl-1-[1-(4-methoxybenzyl)-1H-pyrazol-5-yl]butyl}benzenesulfonamide The compound of example 2 was synthesized from {2-ethyl-1-[1-(4-methoxybenzyl)-1H-pyrazol-5-yl]butyl}amine in a manner similar to that of example 1 but using 4-chlorobenzenesulfonyl chloride as the sulfonyl chloride in step 1D. The product was isolated as white foam in 52% yield.

$^1$H NMR (400 MHz, DMSO-$d_6$): δ 0.61 (t, 3H, J=7.4 Hz), 0.65 (t, 3H, J=7.3 Hz), 0.84-0.99 (m, 2H), 1.17-1.36 (m, 3H), 3.71 (s, 3H), 4.39 (m, 1H), 5.09 (q, 2H, J=15.7 Hz), 6.00 (d, 1H, J=1.5 Hz), 6.87 (d, 2H, sJ=8.6 Hz), 6.99 (d, 2H, J=8.6 Hz), 7.13 (d, 1H, J=1.4 Hz), 7.39 (s, 4H), 8.20 (br s, 1H); Mass Spectrum (+ESI): 462 (M+H)$^+$.

Anal: Calc'd for $C_{23}H_{28}ClN_3O_3S_2$, C, 59.79; H, 6.11; N, 9.10. Found: C, 59.69; H, 5.89; N, 8.95.

EXAMPLE 3

4-Bromo-N-{2-ethyl-1-[1-(4-methoxybenzyl)-1H-pyrazol-5-yl]butyl}benzenesulfonamide The compound of example 3 was synthesized from {2-ethyl-1-[1-(4-methoxybenzyl)-1H-pyrazol-5-yl]butyl}amine in a manner similar to that of example 1 but using 4-bromobenzenesulfonyl chloride as the sulfonyl chloride in step 1D. The product was isolated as a white foam in 67% yield.

$^1$H NMR (400 MHz, DMSO-$d_6$): δ 0.61 (t, 3H, J=7.3 Hz), 0.65 (t, 3H, J=7.3 Hz), 0.84-0.99 (m, 2H), 1.17-1.36 (m, 3H), 3.72 (s, 3H), 4.40 (t, 1H, J=7.5 Hz), 5.05 (q, 2H, J=15.7 Hz), 6.01 (d, 1H, $J_1$=1.5 Hz), 6.87 (d, 2H, J=8.6 Hz), 6.99 (d, 2H, J=8.6 Hz), 7.14 (d, 1H, J=1.7 Hz), 7.32 (d, 2H, J=8.4 Hz), 7.53 (d, 2H, J=8.4 Hz), 8.21 (d, 1H, 8.9 Hz); Mass Spectrum (+ESI): 506 (M+H)$^+$.

Anal: Calc'd for $C_{23}H_{28}BrN_3O_3S_2$ C, 54.55; H, 5.57; N, 8.30. Found: C, 54.73; H, 5.56; N, 8.21.

EXAMPLE 4

5-Chloro-N-{1-[1-(4-methoxybenzyl)-1H-pyrazol-5-yl]ethyl}thiophene-2-sulfonamide

A. 1-[1-(4-Methoxybenzyl)-1H-pyrazol-5-yl]ethanol

The compound of example 4A was synthesized in a manner similar to that of example 1 but using acetaldehyde as the aldehyde in step 1A. The product was isolated as an oil in 31% yield.

$^1$H NMR (400 MHz, DMSO-$d_6$): δ 1.32 (d, 3H, J=6.4 Hz) 3.71 (s, 3H), 4.73-4.77 (m, 1H), 5.25-5.33 (m, 3H), 6.16 (d, 1H, J=1.5 Hz), 6.86 (d, 2H, J=8.6 Hz), 7.09 (d, 2H, J=8.4 Hz), 7.33 (d, 1H, J=1.4 Hz); Mass Spectrum (+ESI): 233 (M+H)$^+$.

B. 5-(1-Azidoethyl)-1-(4-methoxybenzyl)-1H-pyrazole

This compound was prepared from 1-[1-(4-methoxybenzyl)-1H-pyrazol-5-yl]ethanol using the method described in example 1B and isolated as an oil in 56% yield.

$^1$H NMR (400 MHz, DMSO-$d_6$): δ 1.47 (d, 3H, J=6.9 Hz), 3.71 (s, 3H), 4.89 (q, 1H, J=6.7 Hz), 5.31 (m, 2H), 6.39 (d, 1H, J=1.8 Hz), 6.87 (d, 2H, J=8.7 Hz), 7.09 (d, 2H, J=8.6 Hz), 7.46 (d, 1H, J=1.7 Hz); Mass Spectrum (+ESI): 258 (M+H)$^+$.

C. {1-[1-(4-Methoxybenzyl)-1H-pyrazol-5-yl]ethyl}amine

This compound was prepared from 5-(1-azidoethyl)-1-(4-methoxybenzyl)-1H-pyrazole using the method described in example 1C and isolated as an oil in 99% yield.

$^1$H NMR (400 MHz, DMSO-$d_6$): δ 1.19 (d, 3H, 6.6 Hz), 1.75 (bs, 2H), 3.71 (s, 3H), 3.99 (q, 1H, J=6.6 Hz), 5.26 (d, 1H, J=15.6 Hz), 5.36 (d, 1H, J=15.6 Hz), 6.16 (d, 1H, J=1.7 Hz), 6.86 (d, 2H, J=8.6 Hz), 7.06 (d, 2H, J=8.6 Hz), 7.32 (d, 1H, J=1.7 Hz); Mass Spectrum (+ESI): 232 (M+H)$^+$.

D. 5-Chloro-N-{1-[1-(4-methoxybenzyl)-1H-pyrazol-5-yl]ethyl}thiophene-2-sulfonamide This compound was prepared from {1-[1-(4-methoxybenzyl)-1H-pyrazol-5-yl]ethyl} amine using the method described in example 1D and isolated as a colorless oil in 71% yield.

$^1$H NMR (400 MHz, DMSO-$d_6$): δ 1.16 (d, 3H, J=8.4 Hz) 3.71 (s, 3H), 4.59 (m, 1H), 5.23 (m, 2H), 6.15 (d, 1H, J=1.7 Hz), 6.86 (d, 1H, J=8.7) 7.05 (d, 2H, J=8.7 Hz), 7.11 (d, 1H, J=4.0 Hz), 7.21 (d, 1H, J=4.1 Hz), 7.29 (d, 1H, J=1.7 Hz), 8.64 (br s, 1H); Mass Spectrum (−ESI): 410 (M−H)$^-$.

Anal: Calc'd for $C_{17}H_{18}ClN_3O_3S_2$ C, 49.47; H, 4.40; N, 10.20. Found: C, 49.48; H, 4.38; N, 9.87.

EXAMPLE 5

5-Chloro-N-{1-[1-(4-methoxybenzyl)-1H-pyrazol-5-yl]-2-methylpropyl}thiophene-2-sulfonamide

A. 1-[1-(4-Methoxybenzyl)-1H-pyrazol-5-yl]-2-methylpropan-1-ol

The compound of example 5A was synthesized in a manner similar to that of example 1A but using isobutylaldehyde as the aldehyde. The product was isolated a colorless oil in 57% yield.

¹H NMR (400 MHz, DMSO-d₆): δ 0.65 (d, 3H, J=6.7 Hz), 0.89 (d, 3H, J=6.6 Hz), 1.77-1.84 (m, 1H), 3.71 (s, 3H), 4.29 (m, 1H), 5.26 (s, 1H), 5.27 (s, 2H), 6.15 (d, 1H, J=1.7 Hz), 6.85 (d, 2H, J=8.6 Hz), 7.08 (d, 2H, J=8.6 Hz), 7.36 (d, 1H, J=1.7 Hz); Mass Spectrum (+ESI): 261 (M+H)⁺.

B. 5-(1-Azido-2-methylpropyl)-1-(4-methoxybenzyl)-1H-pyrazole

This compound was prepared from 1-[1-(4-methoxybenzyl)-1H-pyrazol-5-yl]-2-methylpropan-1-ol using the method described in example 1B and isolated as an oil in 75% yield.

¹H NMR (400 MHz, DMSO-d₆): δ 0.67 (d, 3H, J=6.7 Hz), 0.96 (d, 3H, J=6.6 Hz), 1.92-1.99 (m, 1H), 3.70 (s, 3H), 4.56 (d, 1H, J=8.7 Hz), 5.34 (m, 2H), 6.35 (d, 1H, J=1.7 Hz), 6.87 (d, 2H, J=8.7 Hz), 7.11 (d, 2H, J=8.7 Hz), 7.51 (d, 1H, J=1.7 Hz); Mass Spectrum (+ESI): 286 (M+H)⁺.

C. {1-[1-(4-Methoxybenzyl)-1H-pyrazol-5-yl]-2-methylpropyl}amine

This compound was prepared from 5-(1-azido-2-methylpropyl)-1-(4-methoxybenzyl)-1H-pyrazole using the method described in example 1C and isolated as an oil in 98% yield.

¹H NMR (400 MHz, DMSO-d₆): δ 0.68 (d, 3H, J=6.7 Hz), 0.84 (d, 3H, J=6.7 Hz), 1.63 (bs, 2H), 1.65-1.72 (m, 1H), 3.61 (d, 1H, J=6.9 Hz), 3.71 (s, 3H), 5.27 (m, 2H), 6.16 (d, 1H, J=1.5 Hz), 6.85 (d, 2H, J=8.6 Hz), 7.06 (d, 2H, J=8.7 Hz), 7.35 (d, 1H, J=1.4 Hz); Mass Spectrum (+ESI): 260 (M+H)⁺.

D. 5-Chloro-N-{1-[1-(4-methoxybenzyl)-1H-pyrazol-5-yl]-2-methylpropyl}thiophene-2-sulfonamide This compound was prepared from {1-[1-(4-methoxybenzyl)-1H-pyrazol-5-yl]-2-methylpropyl}amine using the method described in example 1D and isolated as a white precipitate in 61% yield.

¹H NMR (400 MHz, DMSO-d₆): δ 0.57 (d, 3H, J=6.7 Hz), 0.78 (d, 3H, J=6.7 Hz), 1.72-1.78 (m, 1H), 3.71 (s, 3H), 4.27 (m, 1H), 5.12-5.18 (m, 2H), 6.11 (d, 1H, J=1.7 Hz), 6.87 (d, 2H, J=8.6 Hz), 6.93 (d, 1H, J=4.0 Hz), 6.97 (d, 1H, J=4.0 Hz), 7.11 (d, 2H, J=8.6 Hz), 7.25 (d, 1H, J=1.8 Hz), 8.52 (d, 1H, J=7.9 Hz); Mass Spectrum (+ESI): 440 (M+H)⁺.

Anal: Calc'd for $C_{19}H_{22}ClN_3O_3S_2$ C, 51.87; H, 5.04; N, 9.55. Found: C, 51.80; H, 5.05; N, 9.32.

EXAMPLE 6

5-Chloro-N-{1-[1-(4-methoxybenzyl)-1H-pyrazol-5-yl]butyl}thiophene-2-sulfonamide A. 1-[1-(4-Methoxybenzyl)-1H-pyrazol-5-yl]butan-1-ol The compound of example 6A was synthesized in a manner similar to that of example 1A but using butyraldehyde as the aldehyde. The product was isolated as a yellow oil in 12% yield.

¹H NMR (400 MHz, DMSO-d₆): δ 0.72 (t, 3H, J=7.3 Hz), 1.15-1.36 (m, 2H), 1.43-1.65 (m, 2H), 3.70 (s, 3H), 4.57 (t, 1H), 5.22 (m, 3H), 6.15 (d, 1H, J=1.5 Hz), 6.85 (d, 2H, J=8.6 Hz), 7.06 (d, 2H, J=8.6 Hz), 7.36 (d, 1H, J=1.5 Hz).

B. 5-(1-Azidobutyl)-1-(4-methoxybenzyl)-1H-pyrazole

This compound was prepared from 1-[1-(4-methoxybenzyl)-1H-pyrazol-5-yl]butan-1-ol using the method described in example 1B and isolated as a yellow oil in 57% yield.

¹H NMR (400 MHz, DMSO-d₆): δ 0.77 (t, 3H, J=7.4 Hz), 1.18-1.26 (m, 2H), 1.61-1.75 (m, 2H), 3.67 (s, 3H), 4.7 (t, 1H, J=7.0 Hz), 5.25-5.30 (m, 2H), 6.34 (d, 1H, J=1.7 Hz), 6.83 (d, 2H, J=8.8 Hz), 7.05 (d, 2H, J=8.7 Hz), 7.45 (d, 1H, J=1.8 Hz).

C. {1-[1-(4-Methoxybenzyl)-1H-pyrazol-5-yl]butyl}amine

This compound was prepared from 5-(1-azidobutyl)-1-(4-methoxybenzyl)-1H-pyrazole using the method described in example 1C and isolated as a yellow oil in 99% yield.

¹H NMR (400 MHz, DMSO-d₆): δ 0.72 (t, 3H, 7.3 Hz), 1.13-1.21 (m, 4H), 1.41-1.46 (m, 2H), 3.69 (s, 3H), 3.81 (t, 1H, J=6.8 Hz), 5.23-5.33 (m, 2H), 6.13 (d, 1H, J=1.7 Hz), 6.84 (d, 2H, J=8.8 Hz), 7.04 (d, 2H, J=8.8 Hz), 7.32 (d, 1H, J=1.7 Hz).

D. 5-Chloro-N-{1-[1-(4-methoxybenzyl)-1H-pyrazol-5-yl]butyl}thiophene-2-sulfonamide This compound was prepared from {1-[1-(4-methoxybenzyl)-1H-pyrazol-5-yl]butyl}amine using the method described in example 1D and isolated as a white waxy solid in 46% yield.

¹H NMR (400 MHz, DMSO-d₆): δ 0.62 (t, 3H, J=7.4 Hz), 1.00-1.11 (m, 2H), 1.30-1.37 (m, 1H), 1.42-1.49 (m, 1H), 3.71 (s, 3H), 4.40 (bs, 1H), 5.17-5.23 (m, 2H), 6.11 (d, 1H, J=1.7 Hz), 6.88 (d, 2H, J=8.7 Hz), 7.04 (d, 2H, J=8.6 Hz), 7.05 (d, 1H, J=4.4 Hz), 7.09 (d, 1H, J=4.1 Hz), 7.27 (d, 1H, J=1.5 Hz), 8.61 (br s, 1H); Mass Spectrum (+ESI): 440 (M+H)⁺.

Anal: Calc'd for $C_{19}H_{22}ClN_3O_3S_2$ C, 51.87; H, 5.04; N, 9.55. Found: C, 52.00; H, 5.10; N, 9.48.

EXAMPLE 7

N-[1-(1-Butyl-1H-pyrazol-5-yl)-2-ethylbutyl]-5-chlorothiophene-2-sulfonamide

A. 1-(1-Butyl-1H-pyrazol-5-yl)-2-ethylbutan-1-ol

The compound of example 7A was synthesized in a manner similar to that of example 1A but using 1-butyl-1H-pyrazole as the substituted pyrazole.

¹H NMR (400 MHz, DMSO-d₆): δ 0.75-0.88 (m, 9H), 1.12-1.60 (m, 8H), 1.66-1.74 (m, 1H), 3.98-4.09 (m, 2H), 4.49 (t, 1H, J=6.5 Hz), 5.16 (d, 1H, J=5.7 Hz), 6.06 (d, 1H, J=1.7 Hz), 7.28 (d, 1H, J=1.9 Hz).

B. N-[1-(1-Butyl-1H-pyrazol-5-yl)-2-ethylbutyl]-5-chlorothiophene-2-sulfonamide 1-(1-Butyl-1H-pyrazol-5-yl)-2-ethylbutan-1-ol was converted to 5-(1-azido-2-ethylbutyl)-1-butyl-1H-pyrazole using the procedure described in example 1B. The product was isolated with residual triphenylphosphine.

5-(1-Azido-2-ethylbutyl)-1-butyl-1H-pyrazole was converted to the corresponding amine using the procedure described in example 1C. The product was isolated with residual triphenylphosphine and used in the next step without purification.

The sulfonamide target was prepared from the above amine using the method described in example 1D and isolated as a yellow oil.

$^1$H NMR (400 MHz, DMSO-d$_6$): δ 0.76 (t, 3H, J=7.2 Hz), 0.82 (t, 3H, J=7.4 Hz), 0.88 (t, 3H, J=7.4 Hz), 1.07-1.19 (m, 1H), 1.20-1.33 (m, 4H), 1.34-1.48 (m, 2H), 1.59-1.70 (m, 2H), 3.81-3.94 (m, 2H), 4.44 (m, 1H), 6.09 (d, 1H, J=1.7 Hz), 7.02 (d, 1H, j=4.1 Hz), 7.10 (d, 1H, J=4.0 Hz), 7.19 (d, 1H, J=1.7 Hz), 8.53 (d, 1H, J=9.17 Hz); Mass Spectrum (−ESI): 402 (M−H)$^-$.

Anal: Calc'd for C$_{19}$H$_{22}$ClN$_3$O$_3$S$_2$ C, 50.54; H, 6.49; N, 10.40. Found: C, 50.58; H, 6.65; N, 10.31.

EXAMPLE 8

5-Chloro-N-{2-ethyl-1-[1-(4-hydroxybenzyl)-1H-pyrazol-5-yl]butyl}thiophene-2-sulfonamide To 5-chloro-N-{2-ethyl-1-[1-(4-methoxybenzyl)-1H-pyrazol-5-yl]butyl}thiophene-2-sulfonamide (57.0 mg, 0.121 mmol) in CH$_2$Cl$_2$ (3 mL) at −78° C. was added a solution of boron tribromide (1 M in CH$_2$Cl$_2$, 0.40 mL, 0.40 mmol) dropwise. The reaction mixture was warmed to room temperature gradually over several hours and allowed to stir overnight. Water (10 mL) was added slowly to the mixture. It was then extracted with EtOAc (3×20 mL), dried (Na$_2$SO$_4$) and concentrated. Column chromatography (EtOAc/hex, 3:7) provided 40 mg (72%) of 5-chloro-N-{2-ethyl-1-[1-(4-hydroxybenzyl)-1H-pyrazol-5-yl]butyl}thiophene-2-sulfonamide as a white solid (mp=90-92° C.).

$^1$H NMR (400 MHz, DMSO-d$_6$): δ 0.59 (t, 3H, J=7.4 Hz), 0.67 (t, 3H, J=7.3 Hz), 0.87-0.99 (m, 2H), 1.11-1.32 (m, 3H), 4.43 (bs, 1H), 5.04 (q, 2H, J=15.8 Hz), 6.06 (d, 1H, J=1.8 Hz), 6.66 (d, 2H, J=8.5 Hz), 6.80 (d, 1H, J=4.0 Hz), 6.89 (d, 1H, J=4.0 Hz), 6.90 (d, 2H, J=8.5 Hz), 7.18 (d, 1H, J=1.8 Hz), 8.38 (br s, 1H), 9.34 (s, 1H); Mass Spectrum (−ESI): 452 (M−H)$^-$.

Anal: Calc'd for C$_{20}$H$_{24}$ClN$_3$O$_3$S$_2$ C, 52.91; H, 5.33; N, 9.26. Found: C, 52.67; H, 5.41; N, 8.86.

EXAMPLE 9

5-Chloro-N-(2-ethyl-1-{1-[(4-methylphenyl)sulfonyl]-1H-pyrazol-5-yl}butyl)thiophene-2-sulfonamide

A. 2-Ethyl-1-{1-[(4-methylphenyl)sulfonyl]-1H-pyrazol-5-yl}butan-1-ol

To 1-[(4-methylphenyl)sulfonyl]-1H-pyrazole (0.50 g, 2.26 mmol) [*J Chem. Res.*, Synopses, 10, 327 (1979)] in THF (23 mL) at −78° C. was added a solution of t-butyllithium (1.7 M in pentane, 1.5 mL, 2.49 mmol) dropwise. After 10 min 2-ethylbutyraldehyde (0.31 mL, 2.49 mmol) was added. After 10 min the reaction mixture was quenched with saturated aqueous ammonium chloride (5 mL) and then diluted with H$_2$O (30 mL) and extracted with EtOAc (3×30 mL). The organic extract was dried (Na$_2$SO$_4$) and concentrated. The residue was purified by column chromatography (EtOAc/hexane, 3:7) to give 0.546 g (75%) of 2-ethyl-1-{1-[(4-methylphenyl)sulfonyl]-1H-pyrazol-5-yl}butan-1-ol.

$^1$H NMR (400 MHz, DMSO-d$_6$): δ 0.68 (t, 3H, J=7.5 Hz), 0.92 (t, 3H, J=7.5 Hz), 1.16-1.41 (m, 4H), 1.49-1.57 (m, 1H), 2.38 (s, 3H), 5.25 (t, 1H, J=5.1 Hz), 5.41 (d, 1H, J=5.8 Hz), 6.45 (s, 1H), 7.45 (d, 2H, J=8.1 Hz), 7.74 (s, 1H), 7.79 (d, 2H, J=8.2 Hz); Mass Spectrum (+ESI): 323 (M+H)$^+$.

Anal: Calc'd for C$_{20}$H$_{24}$ClN$_3$O$_3$S$_2$ C, 59.60; H, 6.88; N, 8.69. Found: C, 59.60; H, 6.87; N, 8.62.

B. 5-Chloro-N-(2-ethyl-1-{1-[(4-methylphenyl)sulfonyl]-1H-pyrazol-5-yl}butyl)thiophene-2-sulfonamide To 2-ethyl-1-{1-[(4-methylphenyl)sulfonyl]-1H-pyrazol-5-yl}butan-1-ol (0.250 g, 0.778 mmol) in THF (10 mL) at 0° C. was added triphenylphosphine (0.307 g, 1.17 mmol), diethyl azodicarboxylate (0.18 mL, 1.2 mmol), and diphenylphosphoryl azide (0.25 mL, 1.2 mmol). The reaction mixture was warmed to room temperature and stirred for 20 h. The solvent was removed in vacuo and the resulting residue was purified by column chromatography (EtOAc/hexanes, 15:85) to give 0.260 g (97%) of 5-(1-azido-2-ethylbutyl)-1-[(4-methylphenyl)sulfonyl]-1H-pyrazole with an aromatic impurity as judged by $^1$H NMR. This compound was used in the next step without further purification.

A mixture of 5-(1-azido-2-ethylbutyl)-1-[(4-methylphenyl)sulfonyl]-1H-pyrazole (0.260 g) and 5% Pd/C (16 mg) was stirred under an atm pressure of H$_2$ for 15 h. The mixture was filtered through a plug of Celite and the solvent was removed in vacuo to give 0.207 g of (2-ethyl-1-{1-[(4-methylphenyl)sulfonyl]-1H-pyrazol-5-yl}butyl)amine with an impurity present. This compound was used in the next step without purification.

To (2-ethyl-1-{1-[(4-methylphenyl)sulfonyl]-1H-pyrazol-5-yl}butyl)amine (0.200 g, 0.630 mmol) in CH$_2$Cl$_2$ (10 mL) was added triethylamine (0.18 mL, 1.3 mmol) and 5-chlorothiophene-2-sulfonyl chloride (0.14, 0.76 mmol). After 1 day the reaction mixture was diluted with chloroform (30 mL), washed with H$_2$O (2×30 mL), dried (Na$_2$SO$_4$) and concentrated. Column chromatography (EtOAc/hexane, 3:7) provided 5-chloro-N-(2-ethyl-1-{1-[(4-methylphenyl)sulfonyl]-1H-pyrazol-5-yl}butyl)thiophene-2-sulfonamide (0.104 g, 33%) as a white solid (mp=146-148° C.).

$^1$H NMR (400 MHz, DMSO-d$_6$): δ 0.68 (t, 3H, J=7.4 Hz), 0.94 (t, 3H, J=7.4 Hz), 1.10-1.30 (m, 4H), 1.42-1.57 (m, 1H), 2.41 (s, 3H), 5.28 (dd, 1H, J=4.2, 10.0 Hz), 6.37 (s, 1H), 6.91 (d, 1H, J=4.0 Hz), 6.95 (d, 1H, J=4.0 Hz), 7.51 (d, 2H, J=8.2 Hz), 7.61 (s, 1H), 7.81 (d, 2H, J=8.2 Hz), 8.51 (d, 1H, J=10.2 Hz). Mass Spectrum (−ESI): 500 (M−H)$^-$.

Anal: Calc'd for C$_{20}$H$_{24}$ClN$_3$O$_4$S$_3$ C, 47.85; H, 4.82; N, 8.37. Found: C, 48.00; H, 4.75; N, 8.38.

EXAMPLE 10

5-Chloro-N-{2-ethyl-1-[1-(4-methoxyphenyl)-1H-pyrazol-5-yl]butyl}thiophene-2-sulfonamide

A. 1-(4-Methoxyphenyl)-1H-pyrazole 1-(4-Methoxyphenyl)-1H-pyrazole was prepared as described in the literature (*Tetrahedron Lett.* 39 (1998) 2941-2944). To pyrazole (1.0 g, 14.7 mmol) dissolved in a reaction vessel containing CH$_2$Cl$_2$ (100 mL) and 4 Å molecular sieves (6.0 g) was added 4-methoxyphenylboronic acid (4.5 g, 29.4 mmol), pyridine (3 mL, 36.7 mmol) and copper (II) acetate (4.0 g, 22.0 mmol). The reaction mixture was stirred at room temperature for 72 h and then filtered through a plug of Celite. The filtrate was concentrated in vacuo and then purified by flash chromatography (SiO$_2$, EtOAc/hexane, 1:9, then 1:4) to afford a clear oil in 47% yield.

$^1$H NMR (400 MHz, DMSO-d$_6$) δ 8.35 (m, 1H), 7.72 (m, 2H), 7.66 (m, 1H), 7.02 (m, 2H), 6.47 (m, 1H), 3.77 (s, 3H).

B. 2-Ethyl-1-[1-(4-methoxyphenyl)-1H-pyrazol-5-yl]butan-1-ol

To a chilled reaction vessel at −78° C. containing 1-(4-methoxyphenyl)-1H-pyrazole (*Tetrahedron Lett.* 39(19), 2941-2944, (1998)) (1.096 g, 6.3 mmol) in THF (40 mL) was added a solution of n-butyllithium (2.5M in hexanes, 2.5 mL, 6.4 mmol) dropwise and the mixture was stirred for 1 h. 2-Ethylbutyraldehyde (0.93 mL, 7.5 mmol) was then added dropwise and, after 15 min, the reaction mixture was warmed to room temperature and stirred for 18 h. The reaction mixture was diluted with 0.1N HCl and stirred for 15 min, then poured into a separatory funnel containing EtOAc. The organic layer was separated, dried over $MgSO_4$, filtered and concentrated in vacuo. The resulting oil was purified by column chromatography ($SiO_2$, EtOAc/hexane, 1:4) to yield a pure oil in 68% yield.

$^1$H NMR (400 MHz, DMSO-$d_6$) δ 7.55 (m, 1H), 7.39 (d, 2H, J=8.9 Hz), 7.07 (d, 2H, J=9.0 Hz), 6.37 (m, 1H), 5.26 (d, 1H, J=5.7 Hz), 4.45 (t, 1H, J=6.3 Hz), 3.82 (s, 3H), 1.43 (m, 1H), 1.38 (m, 1H), 1.25 (m, 1H), 1.11 (m, 1H), 0.98 (m, 1H), 0.68 (t, 3H, J=7.5 Hz), 0.50 (t, 3H, J=7.4 Hz).

C. 5-(1-Azido-2-ethylbutyl)-1-(4-methoxyphenyl)-1H-pyrazole

To 2-ethyl-1-[1-(4-methoxyphenyl)-1H-pyrazol-5-yl]butan-1-ol (1.0 g, 3.7 mmol) in THF (35 mL) at 0° C. was added triphenylphosphine (1.5 g, 5.6 mmol), diethyl azodicarboxylate (0.88 mL, 5.6 mmol) and diphenylphosphorylazide (1.2 mL, 5.6 mmol). The reaction mixture was slowly warmed to room temperature and stirred for 18 h. The reaction mixture was diluted with EtOAc and washed twice with 1N HCl. The organic layer was dried ($MgSO_4$), filtered, concentrated in vacuo and the resulting oil was purified by column chromatography ($SiO_2$, EtOAc/hexane, 1:9) to give a clear oil in 80% yield. $^1$H NMR (400 MHz, DMSO-$d_6$) δ 7.66 (d, 1H, J=1.9 Hz), 7.32 (m, 2H), 7.07 (m, 2H), 6.55 (m, 1H), 4.42 (d, 1H, J=8.4 Hz), 3.80 (s, 3H), 1.60 (m, 1H), 1.41 (m, 1H), 1.25 (m, 1H), 1.14 (m, 2H), 0.69 (t, 3H, J=7.4 Hz), 0.60 (t, 3H, J=7.4 Hz).

D. {2-Ethyl-1-[1-(4-methoxyphenyl)-1H-pyrazol-5-yl]butyl}amine

A mixture of 5% Pd/C (300 mg) and 5-(1-azido-2-ethylbutyl)-1-(4-methoxyphenyl)-1H-pyrazole (882 mg, 2.95 mmol) in methanol (30 mL) was shaken on a Parr apparatus under 3 atm of $H_2$ for 18 h. The reaction was filtered through a plug of Celite, washed well with methanol and concentrated in vacuo to yield the amine in 97% yield as an oil.

$^1$H NMR (400 MHz, DMSO-$d_6$) δ 7.49 (m, 1H), 7.36 (d, 2H, J=8.8 Hz), 7.03 (d, 2H, J=8.9 Hz), 6.36 (m, 1H), 3.78 (s, 3H), 1.76 (broad m, 2H), 1.29 (m, 1H), 1.12 (m, 4H), 0.95 (m, 1H), 0.59 (t, 3H, J=7.1 Hz), 0.51 (t, 3H, J=7.1 Hz).

E. 5-Chloro-N-{2-ethyl-1-[1-(4-methoxyphenyl)-1H-pyrazol-5-yl]butyl}thiophene-2-sulfonamide To a stirred solution of the {2-ethyl-1-[1-(4-methoxyphenyl)-1H-pyrazol-5-yl]butyl}amine (0.77 g, 2.8 mmol) in $CH_2Cl_2$ (30 mL) was added triethylamine (0.59 mL, 4.2 mmol) and 5-chlorothiophene-2-sulfonylchloride (0.73 g, 3.4 mmol). The reaction mixture was concentrated in vacuo, diluted with EtOAc, washed twice with 1N HCl, dried ($MgSO_4$), filtered and concentrated in vacuo. The resulting oil was purified by column chromatography ($SiO_2$, EtOAc/hexane, 1:4) to yield a tan solid in 54% yield.

$^1$H NMR (400 MHz, DMSO-$d_6$) δ 8.57 (d, 1H, J=9.5 Hz), 7.41 (m, 1H), 7.24 (m, 3H), 7.10 (m, 3H), 6.31 (m, 1H), 4.50 (m, 1H), 3.83 (s, 3H), 1.31 (m, 1H), 1.19 (m, 2H), 1.06 (m, 2H), 0.59 (t, 3H, J=7.3 Hz), 0.50 (t, 3H, J=7.3 Hz);

IR (solid ATR, cm$^{-1}$) 3270, 3090, 2880, 1515, 1410; MS (ESI+): 454 (M+H)$^+$.

Anal: Calc'd for $C_{20}H_{24}N_3O_3S_2Cl$: C, 52.91; H, 5.33; N, 9.26. Found: C, 53.08; H, 5.33; N, 9.16.

EXAMPLE 11

5-Chloro-N-{2-ethyl-1-[1-(4-hydroxyphenyl)-1H-pyrazol-5-yl]butyl}thiophene-2-sulfonamide To a stirred solution of 5-chloro-N-{2-ethyl-1-[1-(4-methoxyphenyl)-1H-pyrazol-5-yl]butyl}thiophene-2-sulfonamide (0.30 g, 0.66 mmol) in $CH_2Cl_2$ (10 mL) at −78° C. was added a solution of boron tribromide (1.0 M, 0.99 mL, 0.99 mmol) dropwise. After 4 h at −78° C. and 18 h at room temperature, another 1.5 eq $BBr_3$ (0.99 mL) was added at −78° C. The reaction mixture was gradually warmed to room temperature and stirred for 18 h. The reaction mixture was slowly poured into $H_2O$ and extracted with $CH_2Cl_2$ (3x's), dried ($MgSO_4$), filtered, and concentrated in vacuo. The resulting crude solid was purified by column chromatography ($SiO_2$, EtOAc/hexane, 2:3), then precipitated with $Et_2O$/hexane to yield a white solid in 34% yield.

$^1$H NMR (400 MHz, DMSO-$d_6$) δ 9.87 (s, 1H), 8.54 (d, 1H, J=7.9 Hz), 7.38 (d, 1H, J=1.7 Hz), 7.21 (d, 1H, J=4.1 Hz), 7.10 (m, 3H), 6.89 (d, 2H, J=8.9 Hz), 6.29 (m, 1H), 4.49 (m, 1H), 1.31 (m, 1H), 1.16 (m, 1H), 1.11 (m, 1H), 1.08 (m, 2H), 0.59 (t, 3H, J=7.2 Hz), 0.50 (t, 3H, J=7.3 Hz); IR (solid ATR, cm$^{-1}$) 3290, 3180(broad), 2960, 2880, 1520, 1405; Mass Spectrum (+ESI): 440 (M+H)$^+$.

Anal: Calc'd for $C_{19}H_{22}N_3O_3S_2Cl$ C, 51.87; H, 5.04; N, 9.55. Found: C, 51.77; H, 5.04; N, 9.40.

EXAMPLE 12

5-Chloro-N-[2-methyl-1-(1-phenyl-1H-pyrazol-5-yl)propyl]thiophene-2-sulfonamide

A. 2-Methyl-1-(1-phenyl-1H-pyrazol-5-yl)propan-1-ol

This compound was prepared from 1-phenyl-1H-pyrazole and isobutylaldehyde using the method described in example 10B and isolated as a clear oil in 57% yield.

$^1$H NMR (400 MHz, DMSO-$d_6$) δ 7.61 (m, 1H), 7.52 (m, 4H), 7.46 (m, 1H), 6.42 (m, 1H), 5.40 (d, 1H, J=5.65 Hz), 4.19 (m, 1H), 1.82 (m, 1H), 0.86 (d, 3H, J=6.6 Hz), 0.61 (d, 3H, J=6.7 Hz); Mass Spectrum (+ESI): 217 (M+H)$^+$.

B. 5-(1-Azido-2-methylpropyl)-1-phenyl-1H-pyrazole

This compound was prepared from 2-methyl-1-(1-phenyl-1H-pyrazol-5-yl)propan-1-ol using the method described in example 10C and isolated as a clear oil in 98% yield.

$^1$H NMR (400 MHz, DMSO-$d_6$) δ 7.54 (m, 1H), 7.43 (m, 4H), 7.30 (m, 1H), 6.60 (m, 1H), 4.22 (m, 1H), 2.05 (m, 1H), 0.90 (d, 3H, J=6.6 Hz), 0.74 (d, 3H, J=6.7 Hz).

C. 5-Chloro-N-[2-methyl-1-(1-phenyl-1H-pyrazol-5-yl)propyl]thiophene-2-sulfonamide The amine was prepared from 5-(1-azido-2-methylpropyl)-1-phenyl-1H-pyrazole using the method described in example 10D. It was isolated as a colorless oil and used in the next step without purification.

The target compound was prepared from the above amine using the method described in example 10E and isolated as a white solid in 43% yield.

$^1$H NMR (400 MHz, DMSO-$d_6$) δ 8.71 (m, 1H), 7.57 (m, 2H), 7.51 (m, 2H), 7.33 (d, 2H, J=7.1 Hz), 7.14 (d, 1H, J=4.0 Hz), 7.11 (d, 1H, J=4.0 Hz), 6.36 (m, 1H), 4.23 (m, 1H), 1.80 (m, 1H), 0.76 (d, 3H, J=6.6 Hz), 0.63 (d, 3H, J=6.7 Hz); Mass Spectrum (+ESI): 396 (M+H)$^+$. IR (solid ATR, cm$^{-1}$) 3070 (br), 2860, 1500, 1410.

Anal: Calc'd for $C_{17}H_{18}N_3O_2ClS_2$ C, 51.57; H, 4.58; N, 10.61. Found: C, 51.53; H, 4.61; N, 10.55.

EXAMPLE 13

5-Chloro-N-[1-(1-phenyl-1H-pyrazol-5-yl)ethyl]thiophene-2-sulfonamide

A. 1-(1-Phenyl-1H-pyrazol-5-yl)ethanol

This compound was prepared from 1-phenyl-1H-pyrazole and acetaldehyde using the method described in example 10B and isolated as a yellow oil in 54% yield.

$^1$H NMR (400 MHz, DMSO-$d_6$) δ 7.60 (m, 3H), 7.53 (m, 2H), 7.44 (m, 1H), 6.47 (m, 1H), 5.38 (d, 1H, J=5.7 Hz), 4.71 (m, 1H), 1.39 (d, 3H, J=6.4 Hz); Mass Spectrum (+ESI): 189 (M+H$^+$).

B. 5-(1-Azidoethyl)-1-phenyl-1H-pyrazole

This compound was prepared from 1-(1-phenyl-1H-pyrazol-5-yl)ethanol using the method described in example 10C and isolated as a clear oil in 77% yield.

$^1$H NMR (400 MHz, DMSO-$d_6$) δ 7.69 (m, 1H), 7.55-7.43 (m, 4H), 7.31 (m, 1H), 6.63 (m, 1H), 4.70 (m, 1H), 1.53 (d, 3H, J=6.8 Hz).

C. 5-Chloro-N-[1-(1-phenyl-1H-pyrazol-5-yl)ethyl]thiophene-2-sulfonamide 5-(1-Azidoethyl)-1-phenyl-1H-pyrazole was reduced to the amine using the method described in example 10D. The amine was used in the next step without purification. The target compound was prepared from the above amine using the method described in example 10E and isolated as a white solid in 56% yield.

$^1$H NMR (400 MHz, DMSO-$d_6$) δ 8.73 (s, 1H), 7.54 (m, 2H), 7.50 (m, 2H), 7.35 (m, 1H), 7.10 (d, 1H, J=4.0 Hz), 7.08 (d, 1H, J=4.0 Hz), 6.39 (d, 1H, J=1.8 Hz), 4.50 (m, 1H), 1.39 (d, 3H, J=7.0 Hz); IR (solid ATR, cm$^{-1}$) 3050, 2870, 1505; Mass Spectrum (+ESI): 368 (M+H)$^+$.

Anal: Calc'd for $C_{15}H_{14}N_3O_2ClS_2$ C, 48.97; H, 3.84; N, 11.42. Found: C, 49.36; H, 3.72; N, 11.15.

EXAMPLE 14

5-Chloro-N-{2-methyl-1-[1-(4-methylphenyl)-1H-pyrazol-5-yl]propyl}thiophene-2-sulfonamide

A. 2-Methyl-1-[1-(4-methylphenyl)-1H-pyrazol-5-yl]propan-1-ol

This compound was prepared from 1-(4-methylphenyl)-1H-pyrazole (*Tetrahedron Lett.* 39(19): 2941 (1998)) and isobutylaldehyde using the method described in example 10B and isolated as a clear oil in 54% yield.

$^1$H NMR (400 MHz, DMSO-$d_6$) δ 7.58 (s, 1H), 7.39 (d, 2H, J=8.2 Hz), 7.33 (d, 2H, J=8.2 Hz), 6.39 (m, 1H), 5.37 (d, 1H, J=5.6 Hz), 4.16 (m, 1H), 2.38 (s, 3H), 1.83 (m, 1H), 0.86 (d, 3H, J=6.7 Hz), 0.60 (d, 3H, J=6.7 Hz); Mass Spectrum (+ESI): 231 (M+H)$^+$.

B. 5-(1-Azido-2-methylpropyl)-1-(4-methylphenyl)-1H-pyrazole

This compound was prepared from 2-methyl-1-[1-(4-methylphenyl)-1H-pyrazol-5-yl]propan-1-ol using the method described in example 10C and isolated as an oil in 88% yield.

$^1$H NMR (400 MHz, DMSO-$d_6$) δ 7.69 (m, 1H), 7.46 (m, 2H), 7.31 (m, 2H), 6.57 (m, 1H), 4.18 (d, 1H, J=9.0 Hz), 2.37 (s, 3H), 2.04 (m, 1H), 0.91 (d, 3H, J=6.6 Hz), 0.73 (d, 3H, J=6.7 Hz).

C. {2-Methyl-1-[1-(4-methylphenyl)-1H-pyrazol-5-yl]propyl}amine

This compound was prepared from 5-(1-azido-2-methylpropyl)-1-(4-methylphenyl)-1H-pyrazole using the method described in example 10D and isolated as an oil in 53% yield.

$^1$H NMR (400 MHz, DMSO-$d_6$) δ 7.52 (m, 1H), 7.34 (d, 2H, J=8.4 Hz), 7.29 (d, 2H, J=8.2 Hz), 6.35 (m, 1H), 3.50 (d, 1H, J=7.3 Hz), 2.35 (s, 3H), 2.07 (br s, 2H), 1.65 (m, 1H), 0.75 (d, 3H, J=6.6 Hz), 0.58 (d, 3H, J=6.7 Hz).

D. 5-Chloro-N-{2-methyl-1-[1-(4-methylphenyl)-1H-pyrazol-5-yl]propyl}thiophene-2-sulfonamide This compound was prepared from {2-methyl-1-[1-(4-methylphenyl)-1H-pyrazol-5-yl]propyl}amine using the method described in example 10E and isolated as a pale yellow solid in 50% yield.

$^1$H NMR (400 MHz, DMSO-$d_6$) δ 8.69 (d, 1H, J=8.1 Hz), 7.48 (m, 1H), 7.36 (d, 2H, J=7.9 Hz), 7.18 (d, 2H, J=8.2 Hz), 7.13 (d, 1H, J=4.1 Hz), 7.11 (d, 1H, J=4.1 Hz), 6.34 (m, 1H), 4.21 (m, 1H), 2.40 (s, 3H), 1.80 (m, 1H), 0.76 (d, 3H, J=6.7 Hz), 0.63 (d, 3H, J=6.7 Hz); IR (solid ATR, cm$^{-1}$) 2880, 1730, 1460; Mass Spectrum (−ESI): 408 (M−H)$^−$.

Anal: Calc'd for $C_{18}H_{20}N_3O_2ClS_2$ C, 52.74; H, 4.92; N, 0.25. Found: C, 51.55; H, 5.0; N, 9.19.

EXAMPLE 15

5-Chloro-N-{1-[1-(4-fluorophenyl)-1H-pyrazol-5-yl]-2-methylpropyl}thiophene-2-sulfonamide

A. 1-(4-Fluorophenyl)-1H-pyrazole

This compound was prepared from 4-fluorophenylboronic acid using the method described in example 10A and International Patent Publication No. WO 0322008 A1 (2003) and isolated as an oil in 63% yield.

¹H NMR (400 MHz, DMSO-d₆) δ 8.45 (m, 1H), 7.84 (m, 2H), 7.71 (m, 1H), 7.32 (m, 2H), 6.51 (m, 1H).

B. 1-[1-(4-Fluorophenyl)-1H-pyrazol-5-yl]-2-methylpropan-1-ol

This compound was prepared from 1-(4-fluorophenyl)-1H-pyrazole and isobutylaldehyde using the method described in example 10B and isolated as an oil in 45% yield.
¹H NMR (400 MHz, DMSO-d₆) δ 7.61 (m, 1H), 7.57 (m, 2H), 7.37 (t, 2H, J=8.9 Hz), 6.41 (m, 1H), 5.41 (m, 1H), 4.13 (m, 1H), 1.85 (m, 1H), 0.87 (d, 3H, J=6.6 Hz), 0.61 (d, 3H, J=6.8 Hz).

C. 5-(1-Azido-2-methylpropyl)-1-(4-fluorophenyl)-1H-pyrazole

This compound was prepared from 1-[1-(4-fluorophenyl)-1H-pyrazol-5-yl]-2-methylpropan-1-ol using the method described in example 10C and isolated as an oil in 81% yield.
¹H NMR (400 MHz, DMSO-d₆) δ 7.71 (m, 1H), 7.48 (m, 2H), 7.31 (m, 2H), 6.59 (m, 1H), 4.22 (d, 1H, J=8.9 Hz), 2.04 (m, 1H), 0.91 (d, 3H, J=6.6 Hz), 0.74 (d, 3H, J=6.6 Hz).

D. {1-[1-(4-Fluorophenyl)-1H-pyrazol-5-yl]-2-methylpropyl}amine

This compound was prepared from 5-(1-azido-2-methylpropyl)-1-(4-fluorophenyl)-1H-pyrazole using the method described in example 10D and isolated as an oil in 45% yield.
¹H NMR (400 MHz, DMSO-d₆) δ 7.52 (m, 3H), 7.33 (m, 2H), 6.37 (m, 1H), 3.47 (d, 1H, J=7.3 Hz), 2.0 (br s, 2H), 1.66 (m, 1H), 0.76 (d, 3H, J=6.7 Hz), 0.58 (d, 3H, J=6.7 Hz).

E. 5-Chloro-N-{1-[1-(4-fluorophenyl)-1H-pyrazol-5-yl]-2-methylpropyl}thiophene-2-sulfonamide This compound was prepared from {1-[1-(4-fluorophenyl)-1H-pyrazol-5-yl]-2-methylpropyl}amine using the method described in example 10E and isolated as a white solid in 59% yield.
¹H NMR (400 MHz, DMSO-d₆) δ 8.72 (m, 1H), 7.51 (m, 1H), 7.42 (m, 2H), 7.37 (m, 2H), 7.16 (d, 1H, J=4.1 Hz), 7.12 (d, 1H, J=4.1 Hz), 6.35 (m, 1H), 4.16 (m, 1H), 1.80 (m, 1H), 0.77 (d, 3H, J=6.7 Hz), 0.63 (d, 3H, J=6.7 Hz); IR (solid ATR, cm⁻¹) 2890, 1515; Mass Spectrum (−ESI): 412(M−H)⁻.
Anal: Calc'd for $C_{17}H_{17}N_3O_2ClFS_2$ C, 49.33; H, 4.14; N, 10.15. Found: C, 49.41; H, 3.99; N, 9.97.

EXAMPLE 16

5-Chloro-N-{2-methyl-1-[1-(3-methylphenyl)-1H-pyrazol-5-yl]propyl}thiophene-2-sulfonamide

A. 1-(3-Methylphenyl)-1H-pyrazole

This compound was prepared from 3-methylphenylboronic acid using the method described in example 10A and isolated as an oil in 64% yield.
¹H NMR (400 MHz, DMSO-d₆) δ 8.44 (m, 1H), 7.70 (m, 1H), 7.66 (m, 1H), 7.60 (m, 1H), 7.34 (t, 1H, J=7.8 Hz), 7.09 (m, 1H), 6.50 (m, 1H), 2.35 (s, 3H).

B. 2-Methyl-1-[1-(3-methylphenyl)-1H-pyrazol-5-yl]propan-1-ol

This compound was prepared from 1-(3-methylphenyl)-1H-pyrazole using the method described in example 10B and isolated as an oil in 30% yield.
¹H NMR (400 MHz, DMSO-d₆) δ 7.59 (m, 1H), 7.41 (m, 1H), 7.31 (m, 2H), 7.26 (m, 1H), 6.41 (m, 1H), 5.37 (d, 1H, J=5.6 Hz), 4.18 (m, 1H), 2.38 (s, 3H), 1.85 (m, 1H), 0.86 (d, 3H, J=6.6 Hz), 0.61 (d, 3H, J=6.7 Hz); Mass Spectrum (+ESI): 231(M+H)⁺.

C. 5-(1-Azido-2-methylpropyl)-1-(3-methylphenyl)-1H-pyrazole

This compound was prepared from 2-methyl-1-[1-(3-methylphenyl)-1H-pyrazol-5-yl]propan-1-ol using the method described in example 10C and isolated as an oil in 85% yield.
¹H NMR (400 MHz, DMSO-d₆) δ 7.69 (m, 1H), 7.47 (m, 1H), 7.30 (m, 2H), 7.24 (m, 1H), 6.58 (m, 1H), 4.22 (d, 1H, J=8.9 Hz), 2.37 (s, 3H), 2.06 (m, 1H), 0.91 (d, 3H, J=6.6 Hz), 0.74 (d, 3H, J=6.6 Hz).

D. {2-Methyl-1-[1-(3-methylphenyl)-1H-pyrazol-5-yl]propyl}amine

This compound was prepared from 5-(1-azido-2-methylpropyl)-1-(3-methylphenyl)-1H-pyrazole using the method described in example 10D and isolated as an oil in 51% yield.
¹H NMR (400 MHz, DMSO-d₆) δ 7.50 (m, 1H), 7.35 (m, 1H), 7.22 (m, 3H), 6.34 (m, 1H), 3.51 (d, 1H, J=7.3 Hz), 2.33 (s, 3H), 1.99 (br s, 2H), 1.63 (m, 1H), 0.73 (d, 3H, J=6.7 Hz), 0.57 (d, 3H, J=6.7 Hz).

E. 5-Chloro-N-{2-methyl-1-[1-(3-methylphenyl)-1H-pyrazol-5-yl]propyl}thiophene-2-sulfonamide This compound was prepared from {2-methyl-1-[1-(3-methylphenyl)-1H-pyrazol-5-yl]propyl}amine using the method described in example 10E and isolated as a solid in 32% yield.
¹H NMR (400 MHz, DMSO-d₆) δ 8.73 (br s, 1H), 7.51 (m, 1H), 7.44 (t, 1H, J=7.8 Hz), 7.31 (d, 1H, J=7.6 Hz), 7.12 (m, 3H), 7.08 (s, 1H), 6.38 (m, 1H), 4.23 (m, 1H), 2.39 (s, 3H), 1.81 (m, 1H), 0.77 (d, 3H, J=6.7 Hz), 0.64 (d, 3H, J=6.8 Hz). IR (solid ATR, cm⁻¹) 3110, 2970, 1420; Mass Spectrum (−ESI): 408 (M−H)⁻.
Anal: Calc'd for $C_{18}H_{20}N_3O_2ClS_2$ C, 52.74; H, 4.92; N, 10.25. Found: C, 52.71; H, 4.94; N, 9.95.

EXAMPLE 17

5-Chloro-N-[2-ethyl-1-(1-phenyl-1H-pyrazol-5-yl)butyl]thiophene-2-sulfonamide

A. 2-Ethyl-1-(1-phenyl-1H-pyrazol-5-yl)butan-1-ol

This compound was prepared from 1-phenyl-1H-pyrazole using the method described in example 10B and isolated as a clear oil in 75% yield.
¹H NMR (400 MHz, DMSO-d₆) δ 7.60 (m, 1H), 7.52 (m, 4H), 7.48 (m, 1H), 6.42 (m, 1H), 5.33 (d, 1H, J=5.65 Hz), 4.52 (t, 1H, J=6.41 Hz), 1.42 (m, 1H), 1.37 (m, 1H), 1.24 (m, 1H), 1.11 (m, 1H), 0.97 (m, 1H), 0.66 (t, 3H, J=7.4 Hz), 0.56 (t, 3H, J=7.4 Hz). Mass Spectrum (+ESI): 245(M+H)⁺.

B. 5-(1-Azido-2-ethylbutyl)-1-phenyl-1H-pyrazole

This compound was prepared from 2-ethyl-1-(1-phenyl-1H-pyrazol-5-yl)butan-1-ol using the method described in example 10C and isolated as a clear oil in 30% yield.

$^1$H NMR (400 MHz, DMSO-d$_6$) δ 7.71 (m, 1H), 7.55 (m, 2H), 7.44 (m, 2H), 7.32 (m, 2H), 6.59 (m, 1H), 4.53 (d, 1H, J=8.1 Hz), 1.58 (m, 1H), 1.39 (m, 1H), 1.22 (m, 1H), 1.11 (m, 1H), 0.67 (t, 3H, J=7.5 Hz), 0.60 (t, 3H, J=7.5 Hz).

C. [2-Ethyl-1-(1-phenyl-1H-pyrazol-5-yl)butyl]amine

This compound was prepared from 5-(1-azido-2-ethylbutyl)-1-phenyl-1H-pyrazole using the method described in example 10D and isolated as a yellow oil in quantitative yield.

$^1$H NMR (400 MHz, DMSO-d$_6$) δ 7.57 (m, 1H), 7.48 (m, 7H), 7.37 (m, 1H), 6.47 (m, 1H), 3.93 (m, 1H), 1.21 (m, 3H), 0.90 (m, 1H), 0.56 (t, 3H, J=7.2 Hz), 0.48 (t, 3H, J=7.3 Hz).

D. 5-Chloro-N-[2-ethyl-1-(1-phenyl-1H-pyrazol-5-yl)butyl]thiophene-2-sulfonamide This compound was prepared from [2-ethyl-1-(1-phenyl-1H-pyrazol-5-yl)butyl]amine using the method described in example 10E and isolated as a white solid in 47% yield.

$^1$H NMR (400 MHz, DMSO-d$_6$) δ 8.60 (d, 1H, J=9.3 Hz), 7.57 (t, 2H, J=7.6 Hz), 7.51 (m, 1H), 7.47, (m, 1H), 7.34 (m, 2H), 7.22 (d, 1H, J=4.0 Hz), 7.12 (d, 1H, J=4.0 Hz), 6.36 (m, 1H), 4.57 (m, 1H), 1.31 (m, 1H), 1.16 (m, 2H), 1.04 (m, 2H), 0.58 (t, 3H, J=7.3 Hz), 0.48 (t, 3H, J=7.3 Hz); IR (solid ATR, cm$^{-1}$) 3180, 2970, 1500, 1420; Mass Spectrum (+ESI): 424 (M−H)$^-$.

Anal: Calc'd for C$_{19}$H$_{22}$N$_3$O$_2$ClS$_2$ C, 53.82; H, 5.23; N, 9.91. Found: C, 54.07; H, 5.31; N, 9.87.

EXAMPLE 18

5-Chloro-N-(2-ethyl-1-{1-[4-(trifluoromethyl)phenyl]-1H-pyrazol-5-yl}butyl)thiophene-2-sulfonamide

A. 1-[4-(Trifluoromethyl)phenyl]-1H-pyrazole

This compound was prepared from 4-trifluoromethylbenzene boronic acid using the method described in example 10A (*Tetrahedron Lett.* 39(19): 2941 1998) and isolated as a white solid in 41% yield.

$^1$H NMR (400 MHz, DMSO-d$_6$) δ 8.64 (m, 1H), 8.06 (d, 2H, J=8.4 Hz), 7.82 (m, 3H), 6.59 (m, 1H).

B. 2-Ethyl-1-{1-[4-(trifluoromethyl)phenyl]-1H-pyrazol-5-yl}butan-1-ol

This compound was prepared from 1-[4-(trifluoromethyl)phenyl]-1H-pyrazole using the method described in example 10B and isolated as a white solid in 35% yield.

$^1$H NMR (400 MHz. DMSO-d$_6$) δ 7.90 (m, 2H), 7.78 (m, 2H), 7.66 (m, 1H), 6.46 (m, 1H), 5.44 (m, 1H), 4.51 (m, 1H), 1.40 (m, 2H), 1.27 (m, 1H), 1.09 (m, 1H), 0.96 (m, 1H), 0.66 (t, 3H, J=7.3 Hz), 0.56 (t, 3H, J=7.4 Hz).

C. 5-(1-Azido-2-ethylbutyl)-1-[4-(trifluoromethyl)phenyl]-1H-pyrazole

This compound was prepared from 2-ethyl-1-{1-[4-(trifluoromethyl)phenyl]-1H-pyrazol-5-yl}butan-1-ol using the method described in example 10C and isolated as a clear oil in 72% yield.

$^1$H NMR (400 MHz, DMSO-d$_6$) δ 7.93 (m, 2H), 7.79 (m, 1H), 7.73 (m, 3H), 6.67 (m, 1H), 4.65 (d, 1H, J=7.9 Hz), 1.58 (m, 1H), 1.40 (m, 1H), 1.25 (m, 1H), 1.13 (m, 1H), 0.68 (t, 3H, J=7.4 Hz), 0.62 (t, 3H, J=7.4 Hz).

D. (2-Ethyl-1-{1-[4-(trifluoromethyl)phenyl]-1H-pyrazol-5-yl}butyl)amine

This compound was prepared from 5-(1-azido-2-ethylbutyl)-1-[4-(trifluoromethyl)phenyl]-1H-pyrazole using the method described in example 10D and isolated as a clear oil in 67% yield.

$^1$H NMR (400 MHz, DMSO-d$_6$) δ 7.88 (m, 2H), 7.76 (m, 2H), 7.62 (m, 1H), 6.48 (m, 1H), 3.89 (m, 1H), 2.0 (m, 2H), 1.29 (m, 1H), 1.13 (m, 3H), 0.92 (m, 1H), 0.58 (t, 3H, J=7.2 Hz), 0.51 (t, 3H, J=7.2 Hz).

E. 5-Chloro-N-(2-ethyl-1-{1-[4-(trifluoromethyl)phenyl]-1H-pyrazol-5-yl}butyl)thiophene-2-sulfonamide This compound was prepared from (2-ethyl-1-{1-[4-(trifluoromethyl)phenyl]-1H-pyrazol-5-yl}butyl)amine using the method described in example 10E and isolated as a tan solid in 37% yield.

$^1$H NMR (400 MHz, DMSO-d$_6$) δ 8.62 (d, 1H, J=8.0 Hz), 7.93 (d, 2H, J=8.4 Hz), 7.56 (d, 2H, J=8.2 Hz), 7.51 (m, 1H), 7.19 (d, 1H, J=4.0 Hz), 7.06 (d, 1H, J=4.1 Hz), 6.37 (m, 1H), 4.50 (m, 1H), 1.28 (m, 1H), 1.19 (m, 2H), 1.01 (m, 2H), 0.54 (t, 3H, J=7.3 Hz), 0.48 (t, 3H, J=7.3 Hz); IR (solid ATR, cm$^{-1}$) 2880, 1620, 1400; Mass Spectrum (−ESI): 490(M−H)$^-$.

Anal: Calc'd for C$_{20}$H$_{21}$N$_3$O$_2$ClF$_3$S$_2$ C, 48.83; H, 4.30; N, 8.54. Found: C, 49.26; H, 4.36; N, 8.28.

EXAMPLE 19

5-Chloro-N-{2-ethyl-1-[1-(4-fluorobenzyl)-1H-1,2,4-triazol-5-yl]butyl}thiophene-2-sulfonamide

A. 1-(4-Fluorobenzyl)-1H-1,2,4-triazole

To a stirred solution of 1,2,4-triazole (0.803 g, 11.6 mmol) in THF (100 mL) at 0° C. was added 4-fluorobenzyl bromide (2.0 g, 10.6 mmol), then 1,8-diazabicyclo[5.4.0]undec-7-ene (1.9 mL, 12.7 mmol) and the mixture was slowly warmed to room temperature. The solution was concentrated in vacuo, then purified by column chromatography (SiO$_2$, MeOH/EtOAc, 5:95) to yield a white solid in 68% yield.

$^1$H NMR (400 MHz, DMSO-d$_6$) δ 8.60 (s, 1H), 7.93 (s, 1H), 7.29 (m, 2H), 7.13 (m, 2H), 5.36 (s, 2H); IR (solid ATR, cm$^{-1}$) 1610, 1505; Mass Spectrum (+ESI): 178 (M+H)$^+$.

Anal: Calc'd for C$_9$H$_8$N$_3$F C, 61.01; H, 4.55; N, 23.72. Found: C, 61.02; H, 4.39; N, 23.75.

B. 2-Ethyl-1-[1-(4-fluorobenzyl)-1H-1,2,4-triazol-5-yl]butan-1-ol

To a stirred solution of 1-(4-fluorobenzyl)-1H-1,2,4-triazole (0.500 g, 2.82 mmol) in THF (30 mL) at −78° C. was added a solution of n-butyllithium (2.5M in hexanes, 1.1 mL, 2.9 mmol) dropwise. The mixture was stirred at −78° C. for 1.5 h, then 2-ethylbutyraldehyde (0.42 mL, 3.4 mmol) was added. The solution was slowly warmed to room temperature and stirred 18 h. It was then quenched with saturated aqueous NH$_4$Cl and extracted twice with EtOAc. The organic extracts were dried (MgSO$_4$), filtered, concentrated in vacuo and purified by column chromatography (SiO$_2$, EtOAc/hexane, 1:1) to yield an oil in 47% yield.

$^1$H NMR (400 MHz, DMSO-d$_6$) δ 7.86 (s, 1H), 7.28 (m, 2H), 7.15 (m, 2H), 5.72 (d, 1H, J=6.0 Hz), 5.45 (d, 2H, J=9.6 Hz), 4.65 (m, 1H), 1.68 (m, 1H), 1.51 (m, 1H), 1.40 (m, 1H), 1.0 (m, 2H), 0.78 (t, 3H, J=7.4 Hz), 0.63 (t, 3H, J=7.5 Hz).

C. 2-Ethyl-1-[1-(4-fluorobenzyl)-1H-1,2,4-triazol-5-yl]butyl methanesulfonate To a stirred solution of 2-ethyl-1-[1-(4-fluorobenzyl)-1H-1,2,4-triazol-5-yl]butan-1-ol (0.368 g, 1.32 mmol) in pyridine (15 mL) at 0° C. was added methanesulfonyl chloride (0.61 mL, 7.9 mmol) and the solution was slowly warmed to room temperature. The mixture was diluted with H$_2$O, extracted twice with EtOAc and dried (MgSO$_4$), filtered and concentrated in vacuo to give a yellow oil in quantitative yield.

$^1$H NMR (400 MHz, DMSO-d$_6$) δ 8.04 (s, 1H), 7.31 (m, 2H), 7.18 (m, 2H), 5.68 (d, 1H, J=8.6 Hz), 5.48 (s, 2H), 3.08 (s, 3H), 1.81 (m, 1H), 1.56 (m, 1H), 1.39 (m, 1H), 0.94 (m, 2H), 0.77 (t, 3H, J=7.5 Hz), 0.62 (t, 3H, J=7.4 Hz).

D. 5-(1-Azido-2-ethylbutyl)-1-(4-fluorobenzyl)-1H-1,2,4-triazole

To a stirred solution of 2-ethyl-1-[1-(4-fluorobenzyl)-1H-1,2,4-triazol-5-yl]butan-1-ol (0.459 g, 1.42 mmol) in DMF (10 mL) was added sodium azide (0.277 g, 4.26 mmol) and the mixture was heated to reflux for 3 h. After cooling, the reaction mixture was diluted with H$_2$O and extracted with EtOAc twice. The organic extracts were dried (MgSO$_4$), filtered, concentrated in vacuo and purified by column chromatography (SiO$_2$, EtOAc/hexane, 1:9) to yield a clear oil in 67% yield.

$^1$H NMR (400 MHz, DMSO-d$_6$) δ 8.05 (s, 1H), 7.28 (m, 2H), 7.18 (m, 2H), 5.50 (d, 2H, J=3.7 Hz), 4.80 (d, 1H, J=9.0 Hz), 1.87 (m, 1H), 1.59 (m, 1H), 1.40 (m, 1H), 0.98 (m, 2H), 0.80 (t, 3H, J=7.4 Hz), 0.65 (t, 3H, J=7.4 Hz).

E. {2-Ethyl-1-[1-(4-fluorobenzyl)-1H-1,2,4-triazol-5-yl]butyl}amine

To a suspension of 5% Pd/C in EtOAc was added a solution of 5-(1-azido-2-ethylbutyl)-1-(4-fluorobenzyl)-1H-1,2,4-triazole in EtOAc and the mixture was shaken on a Parr apparatus for 2 h under 3 atm of H$_2$. The mixture was filtered through Celite, washed several times with EtOAc, concentrated in vacuo, and purified by column chromatography (SiO$_2$, EtOAc, then, MeOH/EtOAc, 1:9, then 1:4) to yield 68% of the amine.

$^1$H NMR (400 MHz, DMSO-d$_6$) δ 7.85 (s, 1H), 7.25 (m, 2H), 7.14 (m, 2H), 5.41 (d, 2H, J=5.6 Hz), 3.93 (d, 1H, J=7.1 Hz), 2.01 (broad m, 2H), 1.44 (m, 2H), 1.31 (m, 1H), 1.01 (m, 2H), 0.68 (t, 3H, J=7.4 Hz), 0.63 (t, 3H, J=7.4 Hz).

F. 5-Chloro-N-{2-ethyl-1-[1-(4-fluorobenzyl)-1H-1,2,4-triazol-5-yl]butyl}thiophene-2-sulfonamide To a stirred solution of the {2-ethyl-1-[1-(4-fluorobenzyl)-1H-1,2,4-triazol-5-yl]butyl}amine (0.133 g, 0.481 mmol) in CH$_2$Cl$_2$ (10 mL) was added Et$_3$N (0.10 mL, 0.72 mmol) followed by 5-chlorothiophene-2-sulfonyl chloride (0.115 g, 0.529 mmol). The reaction mixture was stirred for 18 h, concentrated in vacuo, partitioned between 0.1N HCl and EtOAc. The organic extracts were dried (MgSO$_4$), filtered and concentrated in vacuo. Column chromatography (SiO$_2$, EtOAc/hexane, 3:7) provided pure material as a yellow solid in 60% yield.

$^1$H NMR (400 MHz, DMSO-d$_6$) δ 8.83 (broad m, 1H), 7.79 (s, 1H), 7.22 (m, 2H), 7.11 (m, 3H), 7.01 (d, 1H, J=4.0 Hz), 5.30 (s, 2H), 4.47 (d, 1H, J=8.4 Hz), 1.56 (m, 1H), 1.39 (m, 1H), 1.29 (m, 1H), 0.79 (m, 1H), 0.61 (m, 1H), 0.59 (t, 3H, J=7.4 Hz), 0.52 (t, 3H, J=7.3 Hz); IR (solid ATR, cm$^{-1}$) 3050, 2870, 1520, 1420; Mass Spectrum (+ESI): 457 (M+H)$^+$.

Anal: Calc'd for C$_{19}$H$_{22}$N$_4$O$_2$S$_2$ClF: C, 49.94; H, 4.85; N, 12.26. Found: C, 50.24; H, 4.84; N, 12.23.

EXAMPLE 20

5-Chloro-N-(2-ethyl-1-{1-[4-(trifluoromethoxy)benzyl]-1H-1,2,4-triazol-5-yl}butyl)thiophene-2-sulfonamide

A. 1-[4-(Trifluoromethoxy)benzyl]-1H-1,2,4-triazole

This compound was prepared from 4-(trifluoromethoxy)benzyl bromide using the method described in example 19A and isolated as a clear oil in 58% yield.

$^1$H NMR (400 MHz, DMSO-d$_6$) δ 8.66 (s, 1H), 7.98 (s, 1H), 7.36 (m, 4H), 5.45 (s, 2H).

B. 2-Ethyl-1-{1-[4-(trifluoromethoxy)benzyl]-1H-1,2,4-triazol-5-yl}butan-1-ol This compound was prepared from 1-[4-(trifluoromethoxy)benzyl]-1H-1,2,4-triazole using the method described in example 19B and isolated as a white solid in 47% yield. $^1$H NMR (400 MHz, DMSO-d$_6$) δ 7.88 (s, 1H), 7.33 (m, 4H), 5.73 (d, 1H, J=5.9 Hz), 5.51 (m, 2H), 4.64 (m, 1H), 1.63 (m, 1H), 1.50 (m, 1H), 1.39 (m, 1H), 0.99 (m, 2H), 0.77 (t, 3H, J=7.4 Hz), 0.61 (t, 3H, J=7.4 Hz).

C. 2-Ethyl-1-{1-[4-(trifluoromethoxy)benzyl]-1H-1,2,4-triazol-5-yl}butyl methanesutfonate This compound was prepared from the 2-ethyl-1-{1-[4-(trifluoromethoxy)benzyl]-1H-1,2,4-triazol-5-yl}butan-1-ol using the method described in example 19C and isolated as a yellow oil in 98% yield.

$^1$H NMR (400 MHz, DMSO-d$_6$) δ 8.07 (m, 1H), 7.37 (m, 4H), 5.67 (m, 1H), 5.55 (m, 2H), 3.10 (s, 3H), 1.81 (m, 1H), 1.55 (m, 1H), 1.39 (m, 1H), 0.92 (m, 2H), 0.77 (t, 3H, J=7.4 Hz), 0.60 (t, 3H, J=7.4 Hz).

D. 5-(1-Azido-2-ethylbutyl)-1-[4-tri-fluoromethoxy)benzyl]-1H-1,2,4-triazole This compound was prepared from the 2-ethyl-1-{1-[4-(trifluoromethoxy)benzyl]-1H-1,2,4-triazol-5-yl}butyl methanesulfonate using the method described in example 19D and isolated as an oil in 72% yield.

$^1$H NMR (400 MHz, DMSO-d$_6$) δ 8.07 (m, 1H), 7.35 (m, 4H), 5.57 (m, 2H), 4.80 (m, 1H), 1.85 (m, 1H), 1.57 (m, 1H), 1.41 (m, 1H), 0.94 (m, 2H), 0.79 (t, 3H, J=7.4 Hz), 0.63 (t, 3H, J=7.4 Hz).

E. (2-Ethyl-1-{1-[4-(trifluoromethoxy)benzyl]-1H-1,2,4-triazol-5-yl}butyl)amine This compound was prepared from 5-(1-azido-2-ethylbutyl)-1-[4-(trifluoromethoxy)benzyl]-1H-1,2,4-triazole using the method described in example 19E and isolated as an oil in 88% yield.

¹H NMR (400 MHz, DMSO-d₆) δ 7.87 (s, 1H), 7.33 (m, 4H), 5.48 (m, 2H), 3.93 (m, 1H), 2.06 (br m, 2H), 1.45 (m, 1H), 1.39 (m, 1H), 1.30 (m, 1H), 1.00 (m, 2H), 0.68 (t, 3H, J=7.3 Hz), 0.62 (t, 3H, J=7.4 Hz).

F. 5-Chloro-N-(2-ethyl-1-{1-[4-(trifluoromethoxy)benzyl]-1H-1,2,4-triazol-5-yl}butyl)thiophene-2-sulfonamide This compound was prepared from (2-ethyl-1-{1-[4-(trifluoromethoxy)benzyl]-1H-1,2,4-triazol-5-yl}butyl)amine using the method described in example 19F and isolated as a yellow solid in 40% yield.

¹H NMR (400 MHz, DMSO-d₆) δ 8.90 (d, 1H, J=8.4 Hz), 7.87 (s, 1H), 7.37 (m, 4H), 7.17 (m, 1H), 7.07 (m, 1H), 5.42 (m, 2H), 4.50 (t, 1H, J=8.4 Hz), 1.60 (m, 1H), 1.42 (m, 1H), 1.32 (m, 1H), 0.77 (m, 1H), 0.71 (m, 1H), 0.62 (t, 3H, J=7.4 Hz), 0.54 (t, 3H, J=7.4 Hz); IR (solid ATR, cm⁻¹) 2970, 1510, 1450, 1340, 1260; Mass Spectrum (−ESI): 521(M−H)⁻.

Anal: Calc'd for $C_{20}H_{22}N_4O_3ClF_3S_2$ C, 45.93; H, 4.24; N, 10.71. Found: C, 46.35; H, 4.11; N, 10.63.

EXAMPLE 21

5-Chloro-N-{2-ethyl-1-[1-(4-methoxybenzyl)-1H-1,2,4-triazol-5-yl]butyl}thiophene-2-sulfonamide A. 1-(4-Methoxybenzyl)-1H-1,2,4-triazole To 1,2,4-triazole (2.0 g, 29 mmol) in THF (80 mL) at 0° C. was added 4-methoxybenzyl chloride (4.0 mL, 29 mmol) and DBU (5.20 mL, 34.7 mmol). The reaction mixture was warmed to room temperature and allowed to stir overnight. The solution was filtered and the filtrate was concentrated. The resulting residue was purified by column chromatography (EtOAc/MeOH, 1:9) to give 3.12 g (57%) of 1-(4-methoxybenzyl)-1H-1,2,4-triazole as a colorless oil.

¹H NMR (400 MHz, DMSO-d₆) δ 3.70 (s, 3H), 5.31 (s, 2H), 6.89 (d, 2H, J=8.7 Hz), 7.23 (d, 2H, J=8.7 Hz), 7.95 (s, 1H), 8.60 (s, 1H).

B. 2-Ethyl-1-[1-(4-methoxybenzyl)-1H-1,2,4-triazol-5-yl]butan-1-ol

To a solution of 1-(4-methoxybenzyl)-1H-1,2,4-triazole (2.12 g, 11.2 mmol) in THF (120 mL) at −78° C. was added a solution of n-butyllithium (2.5 M in hexanes, 4.9 mL, 12.3 mmol) over a period of 20 min. The solution was stirred at −78° C. for 2 h and 45 min. Then 2-ethylbutyraldehyde (0.65 mL, 5.3 mmol) was added. After 1.5 h the reaction mixture was warmed to room temperature, quenched with saturated aqueous ammonium chloride, extracted with EtOAc and dried over Na₂SO₄. After removal of the solvents, the product was purified by recrystallization from EtOAc/hexanes to give 1.75 g (54%) of 2-ethyl-1-[1-(4-methoxybenzyl)-1H-1,2,4-triazol-5-yl]butan-1-ol as a white solid.

¹H NMR (400 MHz, DMSO-d₆) δ 0.62 (t, 3H, J=7.4 Hz), 0.78 (t, 3H, J=7.4 Hz), 0.97-1.01 (m, 2H), 1.38-1.43 (m, 1H), 1.49-1.60 (m, 1H), 1.62-1.72 (m, 1H), 3.70 (s, 3H), 4.63 (dd, 1H, J=6.0, 8.1 Hz), 5.34 (d, 1H, J=15.2 Hz) 5.40 (d, 1H, J=15.2), 5.68 (d, 1H, J=6.0 Hz), 6.86 (d, 2H, J=8.7 Hz), 7.16 (d, 2H, J=8.6 Hz), 7.82 (s, 1H); Mass Spectrum (+ESI): 290 (M+H)⁺.

C. 5-Chloro-N-{2-ethyl-1-[1-(4-methoxybenzyl)-1H-1,2,4-triazol-5-yl]butyl}thiophene-2-sulfonamide To 2-ethyl-1-[1-(4-methoxybenzyl)-1H-1,2,4-triazol-5-yl]butan-1-ol (1.1 g, 3.8 mmol) in pyridine (25 mL) at 0° C. was added methanesulfonyl chloride (0.90 mL, 11.5 mmol). After 20 min the reaction mixture was warmed to room temperature and an additional portion of methanesulfonyl chloride (0.90 mL, 11.5 mmol) was added dropwise. After stirring overnight the reaction mixture was diluted with H₂O (30 mL) and extracted with EtOAc (3×30 mL). The organic extract was dried over Na₂SO₄ and concentrated to give a brown oil, which was used in the next step without further purification.

The crude methanesulfonylate from above was dissolved in DMF (40 mL) and NaN₃ (1.2 g, 18.5 mmol) was added. The mixture was heated to reflux for 3 h and then cooled to room temperature. Water was added and the mixture was extracted with EtOAc, dried over Na₂SO₄ and concentrated. The product was used in the next step without further purification.

To the crude azide from above in ethanol (30 mL) was added 5% Pd/C (200 mg). The mixture was shaken on the Parr apparatus overnight under H₂ atmosphere at 50 psi. The reaction mixture was filtered through a plug of Celite and the filtrate was concentrated. The resulting amine was used in the next step without purification.

To the crude amine from above in CH₂Cl₂ (30 mL) was added 5-chlorothiophene-2-sulfonyl chloride (1.2 g, 5.5 mmol) and triethylamine (0.77 mL, 50.0 mmol). The reaction mixture was stirred overnight. 1N HCl (50 mL) was added and the mixture was extracted with EtOAc (3×50 mL), dried (Na₂SO₄) and concentrated. Column chromatography (SiO₂, EtOAc/hexane, 1:1) provided 0.120 g (7%) of the desired product, mp=136-137° C.

¹H NMR (400 MHz, DMSO-d₆) δ 0.58 (t, 3H, J=7.4 Hz), 0.64 (t, 3H, J=7.5 Hz), 0.71-0.86 (m, 2H), 1.24-1.37 (m, 1H), 1.40-1.47 (m, 1H), 1.62 (br s, 1H), 3.73 (s, 3H), 4.52 (d, 1H, J=8.1 Hz), 5.26 (s, 2H), 6.91 (d, 2H, J=8.7 Hz), 7.05 (d, 1H, J=4.0 Hz), 7.11 (d, 1H, J=4.1 Hz), 7.18 (d, 2H, J=8.7 Hz), 7.81 (s, 1H), 8.87 (br s, 1H); Mass Spectrum (+ESI): 469 (M+H)⁺.

Anal: Calc'd for $C_{20}H_{25}ClN_4O_3S_2$ C, 51.22; H, 5.37; N, 11.95 Found: C, 51.35; H, 5.38; N, 11.87.

EXAMPLE 22

N-[1-(1-Benzyl-1H-1,2,4-triazol-5-yl)-2-ethylbutyl]-5-chlorothiophene-2-sulfonamide A. 1-(1-Benzyl-1H-1,2,4-triazol-5-yl)-2-ethylbutan-1-ol 1-(1-Benzyl-1H-1,2,4-triazol-5-yl)-2-ethylbutan-1-ol was synthesized in a manner similar to that of procedure 21B, but using 1-(phenylmethyl)-1H-1,2,4-triazole as the starting material. The product was isolated as a white solid in 38% yield.

¹H NMR (400 MHz, DMSO-d₆) δ 0.64 (t, 3H, J=7.5 Hz), 0.80 (t, 3H, J=7.5 Hz), 0.98-1.07 (m, 2H), 1.38-1.43 (m, 1H), 1.45-1.59 (m, 1H), 1.65-1.72 (m, 1H), 4.66 (dd, 1H, J=6.0, 8.1 Hz), 5.47 (d, 1H, J=15.6 Hz) 5.52 (d, 1H, J=15.4), 5.72 (d, 1H, J=6.0 Hz), 7.22 (d, 2H, J=8.2 Hz), 7.27-7.38 (m, 3H), 7.89 (s, 1H); Mass Spectrum (+ESI): 260 (M+H)⁺.

B. N-[1-(1-Benzyl-1H-1,2,4-triazol-5-yl)-2-ethylbutyl]-5-chlorothiophene-2-sulfonamide N-[1-(1-benzyl-1H-1,2,4-triazol-5-yl)-2-ethylbutyl]-5-chlorothiophene-2-sulfonamide was prepared by the procedures described in 21C and isolated as a white powder in 14% yield.

$^1$H NMR (400 MHz, DMSO-$d_6$) δ 0.55 (t, 3H, J=7.4 Hz), 0.61 (t, 3H, J=7.4 Hz), 0.70-0.82 (m, 2H), 1.29-1.37 (m, 1H), 1.40-1.46 (m, 1H), 1.60 (br s, 1H), 4.51 (t, 1H, J=8.1 Hz), 5.33 (d, 1H, J=15.9 Hz), 5.37 (d, 1H, J=15.9 Hz), 7.05 (d, 1H, J=4.0 Hz), 7.13 (d, 1H, J=4.1 Hz), 7.22 (d, 2H, J=8.1 Hz), 7.30-7.38 (m, 3H), 7.84 (s, 1H), 8.87 (d, 1H, J=7.9 Hz); Mass Spectrum (+ESI): 439 (M+H)$^+$.

Anal: Calc'd for $C_{19}H_{23}ClN_4O_2S_2$ C, 51.98; H, 5.28; N, 12.76. Found: C, 51.86; H, 5.43; N, 12.68.

EXAMPLE 23

N-[1-(1-Benzyl-1H-1,2,4-triazol-5-yl)-2-methylpropyl]-5-chlorothiophene-2-sulfonamide

A. 1-(1-Benzyl-1H-1,2,4-triazol-5-yl)-2-methylpropan-1-ol 1-(1-Benzyl-1H-1,2,4-triazol-5-yl)-2-methylpropan-1-ol was synthesized in a manner similar to that of procedure 21B but using 1-(phenylmethyl)-1H-1,2,4-triazole and isobutylaldehyde as the starting materials. The product was isolated as a white solid in 71% yield.

$^1$H NMR (400 MHz, DMSO-$d_6$) δ 0.65 (d, 3H, J=6.7 Hz), 0.98 (d, 3H, J=6.7 Hz), 1.99-2.09 (m, 1H), 4.45 (dd, 1H, J=6.1, 7.9 Hz), 5.49 (s, 2H), 5.74 (d, 1H, J=6.1 Hz), 7.23 (d, 2H, J=6.9 Hz), 7.27-7.36 (m, 3H), 7.89 (s, 1H); Mass Spectrum (+ESI): 232 (M+H)$^+$.

B. N-[1-(1-Benzyl-1H-1,2,4-triazol-5-yl)-2-methylpropyl]-5-chlorothiophene-2-sulfonamide N-[1-(1-Benzyl-1H-1,2,4-triazol-5-yl)-2-methylpropyl]-5-chlorothiophene-2-sulfonamide was prepared by the procedures described in 21C and isolated as an off-white powder in 69% yield, mp 138-139° C.

$^1$H NMR (400 MHz, DMSO-$d_6$) δ 0.46 (d, 3H, J=6.7 Hz), 0.85 (d, 3H, J=6.6 Hz), 1.85-2.02 (m, 1H), 4.22-4.26 (m, 1H), 5.38 (d, 2H, J=7.5 Hz), 7.08 (d, 1H, J=4.0 Hz), 7.18 (s, 1H), 7.25 (d, 2H, J=6.9 Hz), 7.31-7.36 (m, 3H), 7.85 (s, 1H), 8.84 (s, 1H); Mass Spectrum (-ESI): 409 (M-H)$^-$.

Anal: Calc'd for $C_{17}H_{19}ClN_4O_2S_2$ C, 49.69; H, 4.66; N, 13.63. Found: C, 49.85; H, 4.71; N, 13.55.

EXAMPLE 24

5-Chloro-N-{2-methyl-1-[1-(4-methylbenzyl)-1H-1,2,4-triazol-5-yl]propyl}thiophene-2-sulfonamide

A. 2-Methyl-1-[1-(4-methylbenzyl)-1H-1,2,4-triazol-5-yl]propan-1-ol

2-Methyl-1-[1-(4-methylbenzyl)-1H-1,2,4-triazol-5-yl]propan-1-ol was synthesized in a manner similar to that of procedure 21B but using 1-(4-methylbenzyl)-1H-1,2,4-triazole and isobutylaldehyde as the starting materials. The product was isolated as a white solid in 66% yield.

$^1$H NMR (400 MHz, DMSO-$d_6$) δ 0.61 (d, 3H, J=6.8 Hz), 0.94 (d, 3H, J=6.6 Hz), 1.98-2.06 (m, 1H), 2.24 (s, 3H), 4.40 (dd, 1H, J=5.9, 8.0 Hz), 5.39 (s, 2H), 5.70 (d, 1H, J=6.03 Hz), 7.08-7.13 (m, 4H), 7.84 (s, 1H); Mass Spectrum (+ESI): 246 (M+H)$^+$.

B. 5-Chloro-N-{2-methyl-1-[1-(4-methylbenzyl)-1H-1,2,4-triazol-5-yl]propyl}thiophene-2-sulfonamide 5-Chloro-N-{2-methyl-1-[1-(4-methylbenzyl)-1H-1,2,4-triazol-5-yl]propyl}thiophene-2-sulfonamide was prepared by the procedures described in 21C and isolated as white powder in 50% yield, mp 124-125° C.

$^1$H NMR (400 MHz, DMSO-$d_6$) δ 0.85 (d, 6H, J=7.8 Hz), 1.97-2.02 (m, 1H), 2.28 (s, 3H), 4.38 (t, 1H, J=7.8 Hz), 5.31 (d, 2H, J=5.7 Hz), 7.08 (d, 1H, J=4.0 Hz), 7.15-7.17 (m, 5H), 7.83 (s, 1H), 8.88 (d, 1H, J=7.0 Hz); Mass Spectrum (+ESI): 425 (M+H)$^+$.

Anal: Calc'd for $C_{18}H_{21}ClN_4O_2S_2$ C, 50.87; H, 4.98; N, 13.18. Found: C, 51.01; H, 4.91; N, 13.15.

EXAMPLE 25

N-[1-(1-Benzyl-1H-1,2,4-triazol-5-yl)ethyl]-5-chlorothiophene-2-sulfonamide

A. 1-(1-Benzyl-1H-1,2,4-triazol-5-yl)ethanol 1-(1-Benzyl-1H-1,2,4-triazol-5-yl)ethanol was synthesized in a manner similar to that of procedure 21B but using 1-(phenylmethyl)-1H-1,2,4-triazole and acetaldehyde as the starting materials. The product was isolated as a white solid in 86% yield.

$^1$H NMR (400 MHz, DMSO-$d_6$) δ 1.84 (d, 3H, J=6.7 Hz), 3.40 (br s, 1H), 5.40 (d, 1H, J=15.6 Hz) 5.52 (d, 1H, J=15.4 Hz), 5.73 (q, 1H, J=6.6 Hz), 7.19-7.35 (m, 5H), 7.98 (s, 1H).

B. N-[1-(1-Benzyl-1H-1,2,4-triazol-5-yl)ethyl]-5-chlorothiophene-2-sulfonamide The target compound was prepared by the procedures described in Example 21C and isolated as a white solid in 30% yield, mp 123-124° C.

$^1$H NMR (400 MHz, DMSO-$d_6$) δ 1.26 (d, 3H, J=6.9 Hz), 4.85 (m, 1H), 5.36 (d, 1H, J=15.6 Hz), 5.44 (d, 1H, J=15.6 Hz), 7.16 (d, 1H, J=4.0 Hz), 7.22 (d, 2H, J=6.9 Hz), 7.31-7.38 (m, 4H), 7.85 (s, 1H), 8.90 (bs, 1H); Mass Spectrum (-ESI): 381 (M-H)$^-$.

Anal: Calc'd for $C_{15}H_{15}ClN_4O_2S_2$ C, 47.05; H, 3.95; N, 14.63. Found: C, 47.01; H, 3.81; N, 14.37.

EXAMPLE 26

5-Chloro-N-{1-[1-(4-methylbenzyl)-1H-1,2,4-triazol-5-yl]ethyl}thiophene-2-sulfonamide

A. 1-[1-(4-Methylbenzyl)-1H-1,2,4-triazol-5-yl]ethanol

1-[1-(4-Methylbenzyl)-1H-1,2,4-triazol-5-yl]ethanol was synthesized in a manner similar to that of the procedure in Example 21B but using 1-(4-methylbenzyl)-1H-1,2,4-triazole and acetaldehyde as the starting materials. The product was isolated as a white solid in 86% yield. $^1$H NMR (400 MHz, DMSO-$d_6$) δ 1.26 (d, 3H, J=6.9 Hz), 2.22 (s, 3H), 3.27 (s, 1H), 4.88-4.94 (m, 1H), 5.66 (d, 2H, J=5.91 Hz), 7.09 (s, 4H), 7.79 (s, 1H).

B. 5-Chloro-N-{1-[1-(4-methylbenzyl)-1H-1,2,4-triazol-5-yl]ethyl}thiophene-2-sulfonamide The target compound was prepared from 1-[1-(4-methylbenzyl)-1H-1,2,4-triazol-5-yl]ethanol by the procedures described in Example 21C and isolated as white solid in 39% yield; mp 116-117° C.

$^1$H NMR (400 MHz, DMSO-$d_6$) δ 1.37 (d, 3H, J=6.5 Hz), 2.28 (s, 3H), 4.80-4.85 (m, 1H), 5.30 (d, 1H, J=15.6 Hz) 5.39 (d, 1H, J=15.4 Hz), 7.10 (d, 2H, J=8.1 Hz), 7.15-7.17 (m, 3H), 7.31 (d, 1H, J=4.1 Hz) 7.83 (s, 1H), 8.89 (br s, 1H); Mass Spectrum (+ESI): 497 (M+H)$^+$.

Anal: Calc'd for $C_{16}H_{17}ClN_4O_2S_2$ C, 48.42; H, 4.32; N, 14.12. Found: C, 48.45; H, 4.33; N, 14.08.

EXAMPLE 27

5-Chloro-N-{2-ethyl-1-[1-(4-methylbenzyl)-1H-1,2,4-triazol-5-yl]butyl}thiophene-2-sulfonamide A. 2-Ethyl-1-[1-(4-methylbenzyl)-1H-1,2,4-triazol-5-yl]butan-1-ol 2-Ethyl-1-[1-(4-methylbenzyl)-1H-1,2,4-triazol-5-yl]butan-1-ol was synthesized in a manner similar to that of the procedure in Example 21B but using 1-(4-methylbenzyl)-1H-1,2,4-triazole as the starting material. The product was isolated as a pale yellow oil in 23% yield.

$^1$H NMR (400 MHz, DMSO-$d_6$) δ 0.65 (t, 3H, J=7.5 Hz), 0.80 (t, 3H, J=7.5 Hz), 1.00-1.07 (m, 2H), 1.39-1.45 (m, 1H), 1.53-1.58 (m, 1H), 1.67-1.71 (m, 1H), 2.28 (s, 3H), 4.65 (dd, 1H, J=6.2, 8.2 Hz), 5.41 (d, 1H, J=15.4 Hz) 5.46 (d, 1H, J=15.4 Hz), 5.70 (d, 1H, J=6.1 Hz), 7.11-7.15 (m, 4H), 7.87 (s, 1H).

B. 5-Chloro-N-{2-ethyl-1-[1-(4-methylbenzyl)-1H-1,2,4-triazol-5-yl]butyl}thiophene-2-sulfonamide 5-Chloro-N-{2-ethyl-1-[1-(4-methylbenzyl)-1H-1,2,4-triazol-5-yl]butyl}thiophene-2-sulfonamide was prepared by the procedure described in Example 21C and isolated as a light yellow solid in 86% yield, mp 103-104° C.

$^1$H NMR (400 MHz, DMSO-$d_6$) δ 0.57 (t, 3H, J=7.3 Hz), 0.63 (t, 3H, J=7.5 Hz), 0.73-0.87 (m, 2H), 1.29-1.35 (m, 1H), 1.41-1.47 (m, 1H), 1.60 (br s, 1H), 2.28 (s, 3H), 4.52 (t, 1H, J=8.2 Hz), 5.29 (s, 2H), 7.05 (d, 1H, J=4.1 Hz), 7.10-7.17 (m, 5H), 7.82 (s, 1H), 8.86 (d, 1H, J=8.2 Hz); Mass Spectrum (+ESI): 453 (M+H)$^+$.

Anal: Calc'd for $C_{20}H_{25}ClN_4O_2S_2$ C, 53.03; H, 5.56; N, 12.37. Found: C, 52.63; H, 5.63; N, 12.21.

EXAMPLE 28

N-[1-(1-Benzyl-1H-imidazol-2-yl)-2-ethylbutyl]-5-chlorothiophene-2-sulfonamide

A. 1-(1-Benzyl-1H-imidazol-2-yl)-2-ethylbutan-1-ol

To a chilled reaction vessel at −45° C. containing 1-benzyl-1H-imidazole (3.0 g, 19.0 mmol) in Et$_2$O (100 mL) was added a solution of n-butyllithium (2.5M in hexanes, 10.8 mL, 26.9 mmol) dropwise. After 30 min, the reaction vessel was cooled to −78° C. and 2-ethylbutyraldehyde (2.8 mL, 22.8 mmol) was added dropwise. The reaction mixture was warmed to 0° C. and stirred for 15 min, then poured into sat. aqueous NH$_4$Cl and extracted with Et$_2$O. The organic layer was washed with H$_2$O, dried over MgSO$_4$, filtered and concentrated in vacuo. The resulting yellow oil was purified by column chromatography (SiO$_2$, EtOAc/hexane, 3:2, then 7:3) to yield a clear oil in 69% yield.

$^1$H NMR (400 MHz, DMSO-$d_6$): δ 7.29 (m, 2H), 7.23 (m, 1H), 7.12 (m, 2H), 7.01 (m, 1H), 6.78 (m, 1H), 5.23 (m, 3H), 4.39 (m, 1H), 1.66 (m, 1H), 1.53 (m, 1H), 1.35 (m, 1H), 0.98 (m, 2H), 0.73 (t, 3H, J=7.47 Hz), 0.54 (t, 3H, J=7.47 Hz).

B. 2-(1-Azido-2-ethylbutyl)-1-benzyl-1H-imidazole

To 1-(1-benzyl-1H-imidazol-2-yl)-2-ethylbutan-1-ol (1.78 g, 6.88 mmol) in THF (50 mL) at 0° C. was added triphenylphosphine (2.71 g, 10.3 mmol), diethyl azodicarboxylate (1.62 mL, 10.3 mmol) and diphenylphosphorylazide (2.22 mL, 10.3 mmol). The reaction mixture was slowly warmed to room temperature and stirred for 18 h. The reaction mixture was diluted with EtOAc and extracted 2 times with 1N HCl. The aqueous layer was washed EtOAc, then basicified with saturated aqueous NaHCO$_3$ and extracted twice with EtOAc. The organic layer was dried over MgSO$_4$, filtered, and concentrated in vacuo. The resulting oil was purified by column chromatography (SiO$_2$, 100% CHCl$_3$, then MeOH/CHCl$_3$/Et$_3$N, 1:98.5:0.5) to yield a pure oil in 30% yield.

$^1$H NMR (400 MHz, DMSO-$d_6$): δ 7.32 (m, 2H), 7.27 (m, 2H), 7.14 (m, 2H), 6.7 (m, 1H), 5.28 (m, 2H), 4.36 (d, 1H, J=9.4 Hz), 1.91 (m, 1H), 1.59 (m, 1H), 1.38 (m, 1H), 0.94 (m, 2H), 0.76 (t, 3H, J=7.48 Hz), 0.59 (t, 3H, J=7.48 Hz).

C. [1-(1-Benzyl-1H-imidazol-2-yl)-2-ethylbutyl]amine

A mixture of 5% Pd/C (200 mg) and 2-(1-azido-2-ethylbutyl)-1-benzyl-1H-imidazole (585 mg, 2.06 mmol) in methanol (25 mL) was shaken on a Parr apparatus for 1 h under 45 psi of H$_2$. The mixture was filtered through a plug of Celite, washed well with methanol and concentrated in vacuo to yield the amine as an oil in 84% yield.

$^1$H NMR (400 MHz, DMSO-$d_6$): δ 7.31 (m, 2H), 7.26 (m, 1H), 7.09 (m, 2H), 7.06 (m, 1H), 6.81 (m, 1H), 5.20 (m, 2H), 3.73 (d, 1H, J=6.5 Hz), 1.60 (br s, 2H), 1.49 (m, 1H), 1.36 (m, 1H), 1.21 (m, 1H), 1.08 (m, 2H), 0.62 (m, 6H).

D. N-[1-(1-Benzyl-1H-imidazol-2-yl)-2-ethylbutyl]-5-chlorothiophene-2-sulfonamide To a stirred solution of [1-(1-benzyl-1H-imidazol-2-yl)-2-ethylbutyl]amine (448 mg, 1.74 mmol) in CH$_2$Cl$_2$ (15 mL) was added triethylamine (0.36 mL, 2.6 mmol) and 5-chlorothiophene-2-sulfonylchloride (453 mg, 2.09 mmol). The mixture was stirred for 3.5 h and then diluted with EtOAc, washed twice with 1N HCl, dried over MgSO$_4$, filtered and concentrated in vacuo. The resulting oil was purified by column chromatography (SiO$_2$, CHCl$_3$, then 1% MeOH/CHCl$_3$ to 2% MeOH/CHCl$_3$) to yield a white solid in 59% yield.

$^1$H NMR (400 MHz, DMSO-$d_6$): δ 8.51 (br s, 1H), 7.29 (m, 2H), 7.26 (m, 1H), 7.08 (m, 2H), 6.99 (m, 3H), 6.75 (s, 1H), 5.05 (m, 2H), 4.33 (d, 1H, J=8.05 Hz), 1.51 (m, 1H), 1.41 (m, 1H), 1.26 (m, 1H), 0.69 (m, 2H), 0.55 (t, 3H, J=7.44 Hz), 0.48 (t, 3H, J=7.38 Hz). IR (solid ATR, cm$^{-1}$) 2970, 1480. Mass Spectrum (ES+): 438 (M+H)$^+$.

Anal: Calc'd for $C_{20}H_{24}ClN_3O_2S_2$ C, 54.84; H, 5.52; N, 9.59 Found: C, 54.64; H, 5.58; N, 9.51.

EXAMPLE 29

5-Chloro-N-{2-ethyl-1-[1-(4-methoxybenzyl)-1H-imidazol-2-yl]butyl}thiophene-2-sulfonamide

A. 2-Ethyl-1-[1-(4-methoxybenzyl)-1H-imidazol-2-yl]butan-1-ol

This compound was prepared from 1-(4-methoxybenzyl)-1H-imidazole using the method described in example 28A to yield a yellow oil in 86% yield.

$^1$H NMR (400 MHz, DMSO-d$_6$): δ 7.11 (d, 2H, J=8.7 Hz), 6.99 (m, 1H), 6.88 (m, 2H), 6.77 (m, 1H), 5.26 (d, 1H, J=6.2 Hz), 5.17 (m, 2H), 4.43 (m, 1H), 3.70 (s, 3H), 1.71 (m, 1H), 1.58 (m, 1H), 1.39 (m, 1H), 1.00 (m, 2H), 0.77 (t, 3H, J=7.5 Hz), 0.59 (t, 3H, J=7.4 Hz).

B. 2-(1-Azido-2-ethylbutyl)-1-(4-methoxybenzyl)-1H-imidazole

This compound was prepared from 2-ethyl-1-[1-(4-methoxybenzyl)-1H-imidazol-2-yl]butan-1-ol using the method described in example 28B to yield a clear oil in 46% yield.

$^1$H NMR (400 MHz, DMSO-d$_6$): δ 7.21 (m, 1H), 7.12 (m, 2H), 6.94 (m, 1H), 6.88 (m, 2H), 5.18 (m, 2H), 4.38 (d, 1H, J=9.4 Hz), 3.70 (s, 3H), 1.94 (m, 1H), 1.60 (m, 1H), 1.39 (m, 1H), 0.98 (m, 2H), 0.79 (t, 3H, J=7.5 Hz), 0.61 (t, 3H, J=7.5 Hz).

C. {2-Ethyl-1-[1-(4-methoxybenzyl)-1H-imidazol-2-yl]butyl}amine

This compound was prepared from 2-(1-azido-2-ethylbutyl)-1-(4-methoxybenzyl)-1H-imidazole using the method described in example 28C to yield an oil in 94% yield.

$^1$H NMR (400 MHz, DMSO-d$_6$): δ 7.08 (d, 2H, J=8.7 Hz), 7.02 (m, 1H), 6.88 (m, 2H), 6.80 (m, 1H), 5.11 (m, 2H), 3.81 (d, 1H, J=6.5 Hz), 3.70 (s, 3H), 2.44 (br m, 2H), 1.49 (m, 1H), 1.41 (m, 1H), 1.21 (m, 1H), 1.09 (m, 2H), 0.68 (m, 6H).

D. 5-Chloro-N-{2-ethyl-1-[1-(4-methoxybenzyl)-1H-imidazol-2-yl]butyl}thiophene-2-sulfonamide This compound was prepared from {2-ethyl-1-[1-(4-methoxybenzyl)-1H-imidazol-2-yl]butyl}amine using the method described in example 28D to yield a white solid in 41% yield.

$^1$H NMR (400 MHz, DMSO-d$_6$): δ 8.57 (br m, 1H), 7.08 (d, 2H, J=8.5 Hz), 7.03 (m, 2H), 6.99 (m, 1H), 6.91 (d, 2H, J=8.9 Hz), 6.77 (m, 1H), 5.02 (m, 2H), 4.40 (d, 1H, J=8.2 Hz), 3.73 (s, 3H), 1.59 (m, 1H), 1.47 (m, 1H), 1.31 (m, 1H), 0.79 (m, 2H), 0.63 (t, 3H, J=7.4 Hz), 0.57 (t, 3H, J=7.4 Hz); IR (solid ATR, cm$^{-1}$) 2980, 1610, 1470; Mass Spectrum (ES+): 468 (M+H)$^+$.

Anal: Calc'd for $C_{21}H_{26}ClN_3O_3S_2$: C, 53.89; H, 5.60; N, 8.98. Found: C, 53.76; H, 5.41; N, 8.87.

EXAMPLE 30

5-Chloro-N-{2-ethyl-1-[1-(4-hydroxybenzyl)-1H-imidazol-2-yl]butyl}thiophene-2-sulfonamide To 5-chloro-N-{2-ethyl-1-[1-(4-methoxybenzyl)-1H-imidazol-2-yl]butyl}thiophene-2-sulfonamide (250 mg, 0.534 mmol) in CH$_2$Cl$_2$ (5 mL) at −78° C. was added a solution of boron tribromide (1M in CH$_2$Cl$_2$, 0.80 mL, 0.80 mmol) dropwise. After 4 h, the reaction mixture was warmed to room temperature and stirred for 18 h. The reaction mixture was then slowly poured into H$_2$O, extracted 3 times with CH$_2$Cl$_2$, dried over MgSO$_4$, filtered and concentrated in vacuo. The material was purified by column chromatography (SiO$_2$, CHCl$_3$, then 2% MeOH/CHCl$_3$) to yield a clear oil in 58% yield.

$^1$H NMR (400 MHz, DMSO-d$_6$): δ 9.45 (s, 1H), 8.55 (m, 1H), 7.02 (s, 2H), 6.97 (d, 3H, J=7.9 Hz), 6.76 (s, 1H), 6.72 (d, 2H, J=8.5 Hz), 4.96 (m, 2H), 4.40 (d, 1H, J=8.2 Hz), 1.60 (m, 1H), 1.48 (m, 1H), 1.32 (m, 1H), 0.78 (m, 2H), 0.63 (t, 3H, J=7.5 Hz), 0.57 (t, 3H, J=7.5 Hz). IR (solid ATR, cm$^{-1}$) 2970, 2940, 2880, 1615, 1595; Mass Spectrum (ES−): 452 (M−H).

Anal: Calc'd for $C_{20}H_{24}ClN_3O_3S_2$: C, 52.91; H, 5.33; N, 9.26. Found: C, 52.45; H, 5.33; N, 9.14.

EXAMPLE 31

N-[1-(1-Benzyl-1H-pyrrol-2-yl)-2-methylpropyl]-5-chlorothiophene-2-sulfonamide

A. 1-(1-Benzyl-1H-pyrrol-2-yl)-2-methylpropan-1-ol

To 1-benzyl-1H-pyrrole-2-carbaldehyde (0.50 g, 2.7 mmol) in THF (20 mL) at 0° C. was added a solution of i-PrMgBr (5.4 mL, 1N in THF, 5.4 mmol). The reaction mixture was warmed to room temperature and after 1.5 h it was quenched with saturated aqueous ammonium chloride, extracted with EtOAc, dried (Na$_2$SO$_4$) and concentrated. Column chromatography (EtOAc/hexanes, 1:4) provided 0.345 g (56%) of 1-(1-benzyl-1H-pyrrol-2-yl)-2-methylpropan-1-ol as an oil.

$^1$H NMR (400 MHz, DMSO-d$_6$): δ 0.66 (d, 3H, J=6.7 Hz), 0.91 (d, 3H, J=6.7 Hz), 1.81-1.88 (m, 1H), 4.04 (dd, 1H, J=5.8, 7.8 Hz), 4.85 (d, 1H, J=5.8 Hz), 5.16 (s, 2H), 5.96-5.99 (m, 2H), 6.69 (m, 1H), 7.05 (d, 2H, J=7.0 Hz), 7.22-7.25 (m, 1H), 7.29-7.32 (m, 2H).

B. 2-(1-Azido-2-methylpropyl)-1-benzyl-1H-pyrrole

This compound was prepared from 1-(1-benzyl-1H-pyrrol-2-yl)-2-methylpropan-1-ol using the method described in example 1B and isolated as an oil in 55% yield.

$^1$H NMR (400 MHz, DMSO-d$_6$): δ 0.67 (d, 3H, J=6.7 Hz), 0.96 (d, 3H, J=6.7 Hz), 1.97-2.05 (m, 1H), 4.13 (d, 1H, J=9.2 Hz), 5.19 (d, 1H, J=16.3 Hz), 5.25 (d, 1H, J=16.3 Hz), 6.11 (t, 1H, J=3.2 Hz), 6.17 (dd, 1H, J=1.7, 3.5 Hz), 6.91 (s, 1H), 7.05 (d, 2H, J=7.2 Hz), 7.24-7.34 (m, 3H).

C. [1-(1-Benzyl-1H-pyrrol-2-yl)-2-methylpropyl]amine

This compound was prepared from 2-(1-azido-2-methylpropyl)-1-benzyl-1H-pyrrole using the method described in example 1C and isolated as an oil in quantitative yield.

$^1$H NMR (400 MHz, DMSO-d$_6$): δ 0.70 (d, 3H, J=6.7 Hz), 0.85 (d, 3H, J=6.7 Hz), 1.55 (bs, 2H), 1.68-1.72 (m, 1H), 4.41 (d, 1H, J=7.0 Hz), 5.15 (d, 1H, J=16.3 Hz), 5.21 (d, 1H, J=16.2 Hz), 5.94-5.99 (m, 2H), 6.67 (s, 1H), 7.02 (d, 2H, J=7.2 Hz), 7.22-7.33 (m, 3H).

D. N-[1-(1-Benzyl-1H-pyrrol-2-yl)-2-methylpropyl]-5-chlorothiophene-2-sulfonamide This compound was prepared from [1-(1-benzyl-1H-pyrrol-2-yl)-2-methylpropyl]amine using the method described in example 1D and isolated as a white solid in 64% yield, mp=102-103° C.

¹H NMR (400 MHz, DMSO-d₆): δ 0.50 (d, 3H, J=6.6 Hz), 0.78 (d, 3H, J=6.6 Hz), 1.71-1.76 (m, 1H), 4.08 (t, 1H, J=8.1 Hz), 4.95 (d, 1H, J=15.9 Hz), 5.01 (d, 1H, J=16.0 Hz), 5.90 (t, 1H, J=3.1 Hz), 5.95 (dd, 1H, J=1.7, 3.5 Hz), 6.62 (s, 1H), 6.93 (d, 1H, J=4.0 Hz), 7.00 (d, 1H, J=4.0 Hz), 7.05 (d, 2H, J=7.2 Hz), 7.25-7.33 (m, 3H), 8.35 (d, 1H, J=8.9 Hz); Mass Spectrum (+ESI): 409 (M+H)⁺.

Anal: Calc'd for $C_{19}H_{21}ClN_2O_2S_2$ C, 55.80; H, 5.18; N, 6.85. Found: C, 56.12; H, 5.33; N, 6.78.

EXAMPLE 32

5-Chloro-N-{1-[1-(4-methoxybenzyl)-1H-pyrrol-2-yl]-2-methylpropyl}thiophene-2-sulfonamide A. 1-(4-Methoxybenzyl)-1H-pyrrole-2-carbaldehyde To pyrrole-2-carboxaldehyde (1.0 g, 10.5 mmol) in THF (60 mL) was added KOtBu (1.2 g, 10.5 mmol), Et₄N⁺I⁻ (100 mg) and 4-methoxybenzyl chloride (1.4 mL, 10.5 mmol). After 1 day saturated aqueous ammonium chloride was added and the mixture was extracted with EtOAc. The organic extract was dried over Na₂SO₄ and concentrated. Column chromatography (EtOAc/hexanes, 1:9) provided 1.48 g (65%) of 1-(4-methoxybenzyl)-1H-pyrrole-2-carbaldehyde as an oil.

¹H NMR (400 MHz, DMSO-d₆): δ 3.68 (s, 3H), 5.42 (s, 2H), 6.24 (dd, 1H, J=2.4, 3.9 Hz), 6.84 (d, 2H, J=8.7 Hz), 7.02 (dd, 1H, J=1.7, 3.9 Hz), 7.10 (d, 2H, J=8.8 Hz), 7.39 (t, 1H, J=2.4 Hz), 9.49 (s, 1H).

B. 1-[1-(4-Methoxybenzyl)-1H-pyrrol-2-yl]-2-methylpropan-1-ol

This compound was prepared from 1-(4-methoxybenzyl)-1H-pyrrole-2-carbaldehyde using the method described in example 31A and isolated as an oil in 49% yield.

¹H NMR (400 MHz, DMSO-d₆): δ 0.67 (d, 3H, J=6.7 Hz), 0.92 (d, 3H, J=6.6 Hz), 1.84-1.88 (m, 1H), 3.72 (s, 3H), 4.08 (dd, 1H, J=6.0, 7.8 Hz), 5.09 (d, 1H, J=15.7 Hz), 5.11 (d, 1H, J=15.7 Hz), 5.93-5.96 (m, 2H), 6.64 (s, 1H), 6.87 (d, 2H, J=8.7 Hz), 7.02 (d, 2H, J=8.7 Hz).

C. 2-(1-Azido-2-methylpropyl)-1-(4-methoxybenzyl)-1H-pyrrole

This compound was prepared from 1-[1-(4-methoxybenzyl)-1H-pyrrol-2-yl]-2-methylpropan-1-ol using the method described in example 1B and isolated as an oil in 47% yield.

¹H NMR (400 MHz, DMSO-d₆): δ 0.68 (d, 3H, J=6.6 Hz), 0.97 (d, 3H, J=6.6 Hz), 1.98-2.05 (m, 1H), 3.72 (s, 3H), 4.18 (d, 1H, J=9.3 Hz), 5.09 (d, 1H, J=15.9 Hz), 5.12 (d, 1H, J=15.7 Hz), 6.08 (t, 1H, J=2.9 Hz), 6.14 (dd, 1H, J=1.5, 3.35 Hz), 6.87-6.89 (m, 3H), 7.02 (d, 2H, J=8.7 Hz).

D. {1-[1-(4-Methoxybenzyl)-1H-pyrrol-2-yl]-2-methylpropyl}amine

This compound was prepared from 2-(1-azido-2-methylpropyl)-1-(4-methoxybenzyl)-1H-pyrrole using the method described in example 1C and isolated as an oil in 95% yield.

¹H NMR (400 MHz, DMSO-d₆): δ 0.68 (d, 3H, J=6.6 Hz), 0.83 (d, 3H, J=6.6 Hz), 1.63-1.72 (m, 1H), 3.3 (bs, 2H), 3.69 (s, 3H), 4.05-4.12 (m, 1H), 5.01-5.11 (m, 2H), 5.90-5.94 (m, 2H), 6.61 (s, 1H), 6.82-6.86 (m, 2H), 6.97 (d, 2H, J=8.7 Hz).

E. 5-Chloro-N-{1-[1-(4-methoxybenzyl)-1H-pyrrol-2-yl]-2-methylpropyl}thiophene-2-sulfonamide This compound was prepared from {1-[1-(4-methoxybenzyl)-1H-pyrrol-2-yl]-2-methylpropyl}amine using the method described in example 1D and isolated as an orange oil in 18% yield.

¹H NMR (400 MHz, DMSO-d₆): δ 0.53 (d, 3H, J=6.6 Hz), 0.80 (d, 3H, J=6.6 Hz), 1.73-1.77 (m, 1H), 3.73 (s, 3H), 4.11 (t, 1H, J=7.8 Hz), 5.87 (s, 2H), 5.86-5.89 (m, 1H), 5.91-5.94 (m, 1H), 6.57 (s, 1H), 6.87 (d, 2H, J=8.7 Hz), 6.92 (d, 1H, J=4.0 Hz), 7.01 (d, 2H, J=8.7 Hz), 8.34 (d, 1H, J=9.0 Hz). Mass Spectrum (+ESI): 439 (M+H)⁺.

Anal: Calc'd for $C_{20}H_{23}ClN_2O_3S_2$ C, 54.72; H, 5.28; N, 6.38. Found: C, 55.28; H, 5.41; N, 6.24.

EXAMPLE 33

N-{1-[1-(Benzyloxy)-1H-pyrazol-5-yl]-2-ethylbutyl}-5-chlorothiophene-2-sulfonamide A. 1-[1-(Benzyloxy)-1H-pyrazol-5-yl]-2-ethylbutan-1-ol To 1-benzyloxy-1H-pyrazole (prepared as described in JOC 60:4996 1995) dissolved in THF (20 mL) and cooled to −78° C. under a nitrogen atmosphere was added a solution of n-butyllithium (1.6 M in hexane, 2.0 mL, 3.2 mmol) via syringe over 10 min. After stirring at the above temperature for 1.25 h, 2-ethyl-butyraldehyde (0.42 mL, 3.4 mmol) was added dropwise. The mixture was then stirred at −78° C. for 1.5 h and quenched by dropwise addition of saturated aqueous ammonium chloride solution (3 mL). The mixture was warmed to ambient temperature and diluted with EtOAc, washed with saturated aqueous NaCl and the organic phase was dried over MgSO₄. Filtration and evaporation of the organic extract produced an oil that was purified on a Biotage column (hexane/EtOAc, 6:1) to give the product as a clear colorless oil (0.565 g, 72%). Mass Spectrum (+ESI): 275 (M+H)⁺.

Anal: Calc'd for $C_{16}H_{22}N_2O_2 \cdot 0.1H_2O$ C, 69.59; H, 8.10; N, 10.14. Found: C, 69.59; H, 7.98; N, 10.43.

B. 5-(1-Azido-2-ethylbutyl)-1-(benzyloxy)-1H-pyrazole

To a stirred mixture of 1-[1-(benzyloxy)-1H-pyrazol-5-yl]-2-ethylbutan-1-ol (0.492 g, 1.79 mmol) in THF (17 mL) at 0° C. under a nitrogen atmosphere was added triphenyl phosphine (0.705 g, 2.69 mmol) followed by diethyl azodicarboxylate (0.42 mL, 2.7 mmol). Diphenyl phosphoryl azide (0.58 mL, 2.7 mmol) was then added over 4 min. The mixture was allowed to attain ambient temperature and stirred for 16 h. The solvent was then evaporated in vacuo producing a crude oil which was purified on a Biotage column (hexane/ethyl acetate, 9:1). This afforded the product as a clear colorless oil (0.36 g, 67%). Mass Spectrum (+ESI): 300 (M+H)⁺.

Anal: Calc'd for $C_{16}H_{21}N_5O$ C, 64.19; H, 7.07; N, 23.39. Found: C, 63.90; H, 6.95; N, 23.40.

C. {1-[1-(Benzyloxy)-1H-pyrazol-5-yl]-2-ethylbutyl}amine 5-(1-Azido-2-ethylbutyl)-1-(benzyloxy)-1H-pyrazole (0.269 g, 0.90 mmol) was dissolved in THF (20 mL). Distilled water (0.40 mL, 22.5 mmol) was added, followed by triphenyl phosphine (0.590 g, 2.25 mmol). The mixture was refluxed for 2 h, cooled to ambient temperature and concentrated in vacuo. This produced a crude oil that was purified on a Biotage column (hexane/EtOAc, 1:1) to afford the product as a colorless oil (0.188 g, 76%). Mass Spectrum (+ESI): 274.2 (M+H)$^+$.

Anal: Calc'd for $C_{16}H_{23}N_3O \cdot 0.35H_2O \cdot 0.1C_4H_8O_2$ C, 68.28; H, 8.56; N, 14.57. Found: C, 67.95; H, 8.16; N, 14.39.

D. N-{1-[1-(Benzyloxy)-1H-pyrazol-5-yl]-2-ethylbutyl}-5-chlorothiophene-2-sulfonamide In a flask containing a mixture of triethylamine (0.045 mL, 0.325 mmol) and {1-[1-(benzyloxy)-1H-pyrazol-5-yl]-2-ethylbutyl}amine (0.081 g, 0.296 mmol) in $CH_2Cl_2$ (1 mL) at ambient temperature was added 5-chlorothiophene-2-sulfonyl chloride (0.064 g, 0.296 mmol). After 16 h the mixture was diluted with $CH_2Cl_2$ (10 mL) and poured into saturated aqueous $NaHCO_3$ (10 mL). The organic phase was separated and washed sequentially with 1N HCl solution, distilled water, brine and then dried over $MgSO_4$, filtered, and concentrated to an oil. Purification by flash chromatography (hexane/EtOAc, 4:1) afforded the product as a solid (0.084 g, 62%). Mass Spectrum (+ESI): 454 (M+H)$^+$.

Anal: Calc'd for $C_{20}H_{24}ClN_3O_3S_2$ C, 52.91; H, 5.33; N, 9.26 Found: C, 53.00; H, 5.45; N, 9.10.

EXAMPLE 34

5-Chloro-N-{(4-fluorophenyl)[1-(4-fluorophenyl)-1H-pyrazol-5-yl]methyl}thiophene-2-sulfonamide This compound was prepared using the method described in example 10, but 4-fluorophenylboronic acid was used as the starting material in step 10A and 4-fluorobenzaldehyde was used as the aldehyde in step 10B. mp=159-160° C.;

Mass Spectrum (–ES): 464.1 (M–H)$^-$;

Anal. Calc'd for $C_{20}H_{14}ClF_2N_3O_2S_2 \cdot 0.10$ $C_6H_{14}$: C, 52.14; H, 3.27; N, 8.85. Found: C, 52.33; H, 3.08; N, 8.83.

EXAMPLE 35

5-Chloro-N-{1-[1-(4-fluorophenyl)-1H-pyrazol-5-yl]-2-phenylethyl}thiophene-2-sulfonamide This compound was prepared using the method described in example 10, but 4-fluorophenylboronic acid was used as the starting material in step 10A and phenylacetaldehyde was used as the aldehyde in step 10B.

Mass Spectrum (–ES): 460.0 (M–H)$^-$.

EXAMPLE 36

4-Chloro-N-[2-ethyl-1-(1-phenyl-1H-pyrazol-5-yl)butyl]benzenesulfonamide

This compound was prepared using the method described in example 10, but 1-phenyl-1H-pyrazole was used as the starting material in step 10B and 4-chlorobenzenesulfonyl chloride was used as the sulfonyl chloride in step 10E. mp 135-136.4° C.; Mass Spectrum (–ES): 416.1 (M–H)$^-$.

Anal. Calc'd for $C_{21}H_{24}ClN_3O_2S$: C, 60.35; H, 5.79; N, 10.05. Found: C, 60.11; H, 6.00; N, 10.11.

EXAMPLE 37

4-Cyano-N-[2-ethyl-1-(1-phenyl-1H-pyrazol-5-yl)butyl]benzenesulfonamide

This compound was prepared using the method described in example 10, but 1-phenyl-1H-pyrazole was used as the starting material in step 10B and 4-cyanobenzenesulfonyl chloride was used as the sulfonyl chloride in step 10E. mp 134.6-136.6° C.; Mass Spectrum (–ES): 407.1 (M–H)$^-$.

Anal. Calc'd for $C_{22}H_{24}N_4O_2S$: C, 64.68; H, 5.92; N, 13.71. Found: C, 64.36; H, 5.86; N, 13.70.

EXAMPLE 38

4,5-Dichloro-N-[2-ethyl-1-(1-phenyl-1H-pyrazol-5-yl)butyl]thiophene-2-sulfonamide This compound was prepared using the method described in example 10, but 1-phenyl-1H-pyrazole was used as the starting material in step 10B and 2,3-dichlorothiophene-5-sulfonyl chloride was used as the sulfonyl chloride in step 10E.

mp 116-119.6° C.; Mass Spectrum (–ES): 458.0 (M–H)$^-$.

EXAMPLE 39

3,4-Dichloro-N-[2-ethyl-1-(1-phenyl-1H-pyrazol-5-yl)butyl]benzenesulfonamide

This compound was prepared using the method described in example 10, but 1-phenyl-1H-pyrazole was used as the starting material in step 10B and 3,4-dichlorobenzenesulfonyl chloride was used as the sulfonyl chloride in step 10E.

mp 56-66° C.; Mass Spectrum (–ES): 452.1 (M–H)$^-$.

Anal. Calc'd for $C_{21}H_{23}Cl_2N_3O_2S$: C, 55.75; H, 5.12; N, 9.29. Found: C, 55.72; H, 5.15; N, 9.08.

EXAMPLE 40

5-Bromo-N-[2-ethyl-1-(1-phenyl-1H-pyrazol-5-yl)butyl]thiophene-2-sulfonamide

This compound was prepared using the method described in example 10, but 1-phenyl-1H-pyrazole was used as the starting material in step 10B and 5-bromothiophene-2-sulphonyl chloride was used as the sulfonyl chloride in step 10E.

mp 120-120.7° C.; Mass Spectrum (–ES): 466.0 (M–H)$^-$.

Anal. Calc'd for $C_{19}H_{22}BrN_3O_2S_2$: C, 48.72; H, 4.73; N, 8.97. Found: C, 48.72; H, 4.31; N, 8.84.

EXAMPLE 41

5-Chloro-N-{(1R)-1-[1-(4-fluorophenyl)-1H-pyrazol-5-yl]-2-methylpropyl}thiophene-2-sulfonamide This compound was isolated from racemate 5-chloro-N-{1-[1-(4-fluorophenyl)-1H-pyrazol-5-yl]-2-methylpropyl}thiophene-2-sulfonamide (example 15) with chiral chromatography (Chiracel AS, 2×25 cm; mobile phase 30% IPA in hexane, flow rate 25 mL/min; retention time 5.6 min.) Mass Spectrum (–ES): 412.1 (M–H)$^-$.

EXAMPLE 42

5-Chloro-N-{(1S)-1-[1-(4-fluorophenyl)-1H-pyrazol-5-yl]-2-methylpropyl}thiophene-2-sulfonamide This compound was isolated from racemate 5-chloro-N-{1-[1-(4-fluorophenyl)-1H-pyrazol-5-yl]-2-methylpropyl}thiophene-2-sulfonamide (example 15) with chiral chromatography (Chiracel AS, 2×25 cm; mobile phase 30% IPA in hexane, flow rate 25 mL/min; retention time 7.1 min.) Mass Spectrum (−ES): 412.1 (M−H)⁻.

EXAMPLE 43

4-Cyano-N-[2-ethyl-1-(1-phenyl-1H-pyrazol-5-yl)butyl]-N-methylbenzenesulfonamide To a suspension of NaH (16.3 nmg, 410 µmol, 60% dispersion in mineral oil) in THF (300 µL) at 0° C. was added a solution of 4-cyano-N-[2-ethyl-1-(1-phenyl-1H-pyrazol-5-yl)butyl]benzenesulfonamide (example 37, 140 mg, 340 µmol) in THF (600 µL). The reaction mixture was warmed to room temperature, and after 20 min iodomethane (45 µL, 714 µmol) was added. The mixture was allowed to stir overnight. TLC indicated that the reaction was not complete. Additional aliquots of NaH and iodomethane were added until the reaction was driven to completion. The mixture was then quenched with $H_2O$ and extracted with EtOAc twice. The organic extracts were dried ($MgSO_4$) and concentrated. Column chromatography (EtOAc/hexanes, 1:1) provided 89 mg (57% yield) of the title compound as a glassy yellow solid. mp 37.8-54° C.; Mass Spectrum (ES): 481.1;

Anal. Calc'd for $C_{23}H_{26}N_4O_2S$: C, 65.38; H, 6.20; N, 13.26. Found: C, 65.48; H, 6.38; N, 12.96.

EXAMPLE 44

4-Chloro-N-[2-ethyl-1-(1-phenyl-1H-pyrazol-5-yl)butyl]-N-methylbenzenesulfonamide This compound was prepared using the method described in example 43, but 4-chloro-N-[2-ethyl-1-(1-phenyl-1H-pyrazol-5-yl)butyl]benzenesulfonamide (example 36) was used as the starting material. mp 86.5-89° C.; Mass Spectrum (−ES): 432.1 (M−H)⁻.

Anal. Calc'd for $C_{22}H_{26}ClN_3O_2S$: C, 61.17; H, 6.07; N, 9.73. Found: C, 61.12; H, 5.85; N, 9.55.

EXAMPLE 45

4,5-Dichloro-N-[2-ethyl-1-(1-phenyl-1H-pyrazol-5-yl)butyl]-N-methylthiophene-2-sulfonamide This compound was prepared using the method described in example 43, but 4,5-dichloro-N-[2-ethyl-1-(1-phenyl-1H-pyrazol-5-yl)butyl]thiophene-2-sulfonamide (example 38) was used as the starting material. mp 99-100.4° C.; Mass Spectrum (−ES): 472.0 (M−H)⁻.

Anal. Calc'd for $C_{20}H_{23}Cl_2N_3O_2S_2$: C, 50.85; H, 4.91; N, 8.89. Found: C, 50.97; H, 4.61; N, 8.79.

EXAMPLE 46

5-Chloro-N-[2-ethyl-1-(1-phenyl-1H-pyrazol-5-yl)butyl]-N-methylthiophene-2-sulfonamide This compound was prepared using the method described in example 43, but 5-chloro-N-[2-ethyl-1-(1-phenyl-1H-pyrazol-5-yl)butyl]thiophene-2-sulfonamide (example 17) was used as the starting material. mp 125.8-127.6° C.; Mass Spectrum (−ES): 438.1 (M−H)⁻.

Anal. Calc'd for $C_{20}H_{24}ClN_3O_2S_2$: C, 54.84; H, 5.52; N, 9.59. Found: C, 55.16; H, 5.25; N, 9.34.

EXAMPLE 47

3,4-Dichloro-N-[2-ethyl-1-(1-phenyl-1H-pyrazol-5-yl)butyl]-N-methylbenzenesulfonamide This compound was prepared using the method described in example 43, but 3,4-dichloro-N-[2-ethyl-1-(1-phenyl-1H-pyrazol-5-yl)butyl]benzenesulfonamide (example 39) was used as the starting material. mp 102.1-104.1° C.; Mass Spectrum (−ES): 466.2 (M−H)⁻.

Anal. Calc'd for $C_{22}H_{25}Cl_2N_3O_2S$: C, 56.65; H, 5.40; N, 9.01. Found: C, 56.64; H, 5.23; N, 8.81.

EXAMPLE 48

5-Bromo-N-[2-ethyl-1-(1-phenyl-1H-pyrazol-5-yl)butyl]-N-methylthiophene-2-sulfonamide This compound was prepared using the method described in example 43, but 5-bromo-N-[2-ethyl-1-(1-phenyl-1H-pyrazol-5-yl)butyl]thiophene-2-sulfonamide (example 40) was used as the starting material. mp 115.6-118° C.;

Mass Spectrum (−ES): 482.1 (M−H)⁻.

EXAMPLE 49

Repressor Release Assay (ROA)

The compound is considered active in RRA if it leads to at least a 1.5 fold increase in APPI as measured by an increase in luciferase activity at 20 µg/mL and is non-toxic. Shuey, D. J., Sheiffele, P., Jones, D., Cockett, M. I., and Quinet, E. M. (1999) Repressor release: a useful tool for monitoring amyloid precursor protein (APP) proteolysis in mammalian cells. *Society for Neuroscience Abstracts*, Vol. 25, 29th Annual Meeting of Society for Neuroscience, Miami Beach, Fla., Oct. 23-28, 1999. See Table 3.

A. Cell Culture

CHO—K1 cells are cultured in whole DMEM media (DMEM—High Glucose with 10% fetal bovine serum, 1% Non-essential Amino Acids, and 1% Penicillin-Streptomycin) at 37° C. with 5% $CO_2$. Two million cells are plated into 10-cm dishes 24 hrs prior to transfection.

Transient transfections are completed as recommended by Gibco BRL using their Lipofectamine Plus system. First, 6 µg of pRSVO-luc and 6 µg of APP-lacI construct DNA are added to 460 µL Opti-Mem transfection media and incubated with 30 µL Plus reagent for 15 minutes. Then, a lipid mixture of 40 µL Lipofectamine reagent and 460 µL Opti-Mem transfection media is incubated with the DNA-Plus reagent mixture for 15 minutes. During the DNA-lipid incubation, the CHO—K1 cells are washed once and covered in 5.0 mL DMEM media without Penicillin-Streptomycin. The DNA-lipid preparation is then layered onto these cells and incubated at 37° C. overnight.

One and one half million transfected cells per well (100 μL total volume) are plated into sterile, opaque Packard 96-well Cultur-Plates in clear DMEM whole media (DMEM—without phenol red) and incubated at 37° C. with 5% $CO_2$ for 3-5 hours.

B. Compound Dilution

Compounds are diluted using two different protocols; one protocol is used for compounds supplied neat (weighed powder in vial) and the other protocol is used for compounds supplied in solution (20 mM in DMSO in 96-well plates). For both protocols, 25 mM Hepes and 25 mM Hepes/1% DMSO are prepared fresh to be used as diluent. The Hepes/DMSO is used as the diluent control on all experimental plates.

The following Table 1 depicts the steps for compound dilution (the last step is the addition of compound to cells/media in tissue culture plate):

TABLE 1

|  | Concentration | Dilution |
| --- | --- | --- |
| Stock Solution | 10 mg/mL | x mg compound (vial) diluted with 100% DMSO |
| Dilution 1 | 1 mg/mL | 20 μL stock solution 180 μL 25 mM Hepes |
| Dilution 2 | 200 μg/mL | 60 μL Dilution 1 240 μL 25 mM Hepes |
| Dilution 3 (in Cell Plate) | 20 μg/mL | 11.3 μL Dilution 2 (in 100 μL cells/well) |

Because some compounds arrive in 96-well format at 20 mM, the following Table 2 represents the protocol for their dilution (an average molecular weight of these compounds was used to calculate these dilutions and as above, the last step is the addition of compound to cells/media in tissue culture plate):

TABLE 2

|  | Concentration | Dilution |
| --- | --- | --- |
| Stock Solution (original conc.) | — | 20 mM Solution |
| Dilution 1 | ~200 μg/mL | 6 μL stock solution 194 μL 25 mM Hepes |
| Dilution 2 (in Cell Plate) | ~20 μg/mL | 11.3 μL Dilution 2 (in 100 μL cells/well) |

Once compounds are diluted, they are applied in duplicate on cells in tissue culture plates (prepared above). Cells are incubated with compound at 37° C. with 5% $CO_2$ for an additional 36-48 hours.

C. Assay Measurement

Luciferase assays (LucLite reagent, Packard) are performed and are read on a Packard TopCount instrument. Media is removed from each 96-well plate and replaced with 100 μL PBS per well (with $Mg^{2+}$ and $Ca^{2+}$). An equal volume (100 μL) of the LucLite lysis/substrate buffer is added to each well and the plates are sealed and mixed in the dark on a rotary shaker for 15-30 minutes at room temperature. Luciferase readings are then taken on the TopCount instrument. Measurements are expressed as relative light units (RLU) and are calculated and analyzed in MS Excel as follows:

D. Analysis of Data

Fold Increase: amount of luciferase activity (measured in relative light units) over diluent control.

SEM: standard error of the mean for fold increase.

Activity: A compound is considered active if it results in at least a 1.5 fold increase in luciferase activity at 20 μg/mL.

Toxicity: determined by loss of signal (<0.75 fold increase).

E. Standard Beta Amyloid Inhibitor

The reference gamma secretase inhibitor DAPT (LY374973, AN37124: Dovey, H. F. et al., *J. Neurochem.* 76: 173-181 (2001)) was prepared as outlined in International Patent Publication No. WO 98/22494 and tested in RRA and exhibited a 18.5-28.1 fold increase in luciferase activity at 20 μg/mL.

EXAMPLE 50

Aβ40/42 ELISA Assay

Compounds are diluted from DMSO stocks to 2 μM and below in a cell culture medium. Compounds are then applied to CHO cells carrying the APP-REP-NL plasmid [Sudhir et. al, J. Biolog. Chem. 267:25602-25608 (1992)] for a period of 22 hours. After the conditioning period, medium is collected, diluted in assay buffer containing protein, and samples, controls, and synthetic peptide standards are incubated on a prepared ELISA plate. Using a sandwich ELISA with antibodies specifically directed against the carboxyl terminus of beta amyloid 40 or 42 (analogous to the method reported by Haugabook et al., J. Neurosci. Methods 108:171-179 (2001) but using goat anti-mouse IgG1 (source: Southern Biotech) as the anchor, 6E10 as the capture antibody (Source: SENETEK), rabbit antiAβ40 and antiAβ42 (source: QCB) and APL-donkey anti-rabbit IgG (H+L, source: Southern Biotech) as the detection antibody), the effect of the compound treatment on the cellular production of extracellular beta amyloid is quantified. Cells treated with compound are subsequently incubated in cell culture medium containing MTS-formazan. After a short incubation period, MTS/medium containing plates are read in a spectrophotometer to determine the extent to which compound toxicity affected the cell's metabolism and ability to synthesize beta amyloid.

Materials for the Assay:

A. Test Samples: compound samples are supplied as 20 mM stock solutions in a 100% DMSO solution.

B. APP-REP-NL cells: Qualified cell lines are carried from week to week using 1:100 dilutions and are cultured in DMEM supplemented with 1× antibiotic/antimycotic, 200 ug/ml of G418 antibiotic, and 10% certified fetal calf serum. Cells are also banked in liquid nitrogen. Periodically, beta amyloid production is assessed, and cells are either kept in culture or replaced with progenitors at full expression.

C. Antibodies: From certified lots that have already been qualified in this assay. Antibodies are stored in small frozen aliquots at −80° C. that are thawed and used.

D. Reagents: are of the highest quality available. Certain reagents are "lot specific" and only reagents from that specific manufacturer and lot may be used.

E. Plasticware: is of the highest quality available.

Criteria for Activity

A compound is considered active if it has an $EC_{50}$ for Aβ40 reduction of <100 μM and no toxicity at doses in the vicinity of the $EC_{50}$.

TABLE 3

| Ex # | RRA data* | Aβ40 EC50 (μM) | Aβ42 EC50 (μM) | Name |
|---|---|---|---|---|
| 1 | 7.8 | 1.0 | 1.0 | 5-Chloro-N-{2-ethyl-1-[1-(4-methoxybenzyl)-1H-pyrazol-5-yl]butyl}thiophene-2-sulfonamide |
| 2 | 11.3 | 6.4 | 13.0 | 4-Chloro-N-{2-ethyl-1-[1-(4-methoxybenzyl)-1H-pyrazol-5-yl]butyl}benzenesulfonamide |
| 3 | 5.9 | 6.8 | 10.0 | 4-Bromo-N-{2-ethyl-1-[1-(4-methoxybenzyl)-1H-pyrazol-5-yl]butyl}benzenesulfonamide |
| 4 | 2.3 | 1.8 | 1.3 | 5-Chloro-N-{1-[1-(4-methoxybenzyl)-1H-pyrazol-5-yl]ethyl}thiophene-2-sulfonamide |
| 5 | 3.5 | 1.1 | 0.9 | 5-Chloro-N-{1-[1-(4-methoxybenzyl)-1H-pyrazol-5-yl]-2-methylpropyl}thiophene-2-sulfonamide |
| 6 | 4.7 | 1.5 | 1.4 | 5-Chloro-N-{1-[1-(4-methoxybenzyl)-1H-pyrazol-5-yl]butyl}thiophene-2-sulfonamide |
| 7 | 5.4 | 2.4 | 2.7 | N-[1-(1-Butyl-1H-pyrazol-5-yl)-2-ethylbutyl]-5-chlorothiophene-2-sulfonamide |
| 8 | 4.5 | nd | nd | 5-Chloro-N-{2-ethyl-1-[1-(4-hydroxybenzyl)-1H-pyrazol-5-yl]butyl}thiophene-2-sulfonamide. |
| 9 | *** | 3.0 | 4.5 | 5-Chloro-N-(2-ethyl-1-{1-[(4-methylphenyl)sulfonyl]-1H-pyrazol-5-yl}butyl)thiophene-2-sulfonamide |
| 10 | 1.7 | 4.0 | 10.1 | 5-Chloro-N-{2-ethyl-1-[1-(4-methoxyphenyl)-1H-pyrazol-5-yl]butyl}thiophene-2-sulfonamide |
| 11 | 3.0 | 1.0 | 2.7 | 5-Chloro-N-{2-ethyl-1-[1-(4-hydroxyphenyl)-1H-pyrazol-5-yl]butyl}thiophene-2-sulfonamide |
| 12 | *** | 1.4 | 3.3 | 5-Chloro-N-[2-methyl-1-(1-phenyl-1H-pyrazol-5-yl)propyl]thiophene-2-sulfonamide |
| 13 | 6.4 | 4.8 | 5.1 | 5-Chloro-N-[1-(1-phenyl-1H-pyrazol-5-yl)ethyl]thiophene-2-sulfonamide |
| 14 | 17.7 | 1.2 | 1.2 | 5-Chloro-N-{2-methyl-1-[1-(4-methylphenyl)-1H-pyrazol-5-yl]propyl}thiophene-2-sulfonamide |
| 15 | 2.8 | 4.0 | 5.1 | 5-Chloro-N-{1-[1-(4-fluorophenyl)-1H-pyrazol-5-yl]-2-methylpropyl}thiophene-2-sulfonamide |
| 16 | 4.0 | 3.5 | 4.4 | 5-Chloro-N-{2-methyl-1-[1-(3-methylphenyl)-1H-pyrazol-5-yl]propyl}thiophene-2-sulfonamide |
| 17 | 0.2 1.5 | 4.2 | 10.0 | 5-Chloro-N-[2-ethyl-1-(1-phenyl-1H-pyrazol-5-yl)butyl]thiophene-2-sulfonamide |
| 18 | 2.3 | 5.9 | 10.7 | 5-Chloro-N-(2-ethyl-1-{1-[4-(trifluoromethyl)phenyl]-1H-pyrazol-5-yl}butyl)thiophene-2-sulfonamide |
| 19 | 3.9 | — | — | 5-Chloro-N-{2-ethyl-1-[1-(4-fluorobenzyl)-1H-1,2,4-triazol-5-yl]butyl}thiophene-2-sulfonamide |
| 20 | 9.8 | 2.4 | 4.3 | 5-Chloro-N-(2-ethyl-1-{1-[4-(trifluoromethoxy)benzyl]-1H-1,2,4-triazol-5-yl}butyl)thiophene-2-sulfonamide |
| 21 | 10.8 | 1.4 | 3.1 | 5-Chloro-N-{2-ethyl-1-[1-(4-methoxybenzyl)-1H-1,2,4-triazol-5-yl]butyl}thiophene-2-sulfonamide |
| 22 | 7.2 | 1.5 | 1.5 | N-[1-(1-Benzyl-1H-1,2,4-triazol-5-yl)-2-ethylbutyl]-5-chlorothiophene-2-sulfonamide |
| 23 | 1.8 | 5.2 | 13.2 | N-[1-(1-Benzyl-1H-1,2,4-triazol-5-yl)-2-methylpropyl]-5-chlorothiophene-2-sulfonamide |
| 24 | 1.8 | 6.0 | 11.0 | 5-Chloro-N-{2-methyl-1-[1-(4-methylbenzyl)-1H-1,2,4-triazol-5-yl]propyl}thiophene-2-sulfonamide |
| 25 | 6.6 | 42.5 | 90 | N-[1-(1-Benzyl-1H-1,2,4-triazol-5-yl)ethyl]-5-chlorothiophene-2-sulfonamide |
| 26 | 5.6 | 9.6 | 15.5 | 5-Chloro-N-{1-[1-(4-methylbenzyl)-1H-1,2,4-triazol-5-yl]ethyl}thiophene-2-sulfonamide |
| 27 | 13 | 2.7 | 6.2 | 5-Chloro-N-{2-ethyl-1-[1-(4-methylbenzyl)-1H-1,2,4-triazol-5-yl]butyl}thiophene-2-sulfonamide |
| 28 | 1.5 | 19.4 | nd | N-[1-(1-Benzyl-1H-imidazol-2-yl)-2-ethylbutyl]-5-chlorothiophene-2-sulfonamide |
| 29 | 1.9 | 50.7 | 52.5 | 5-Chloro-N-{2-ethyl-1-[1-(4-methoxybenzyl)-1H-imidazol-2-yl]butyl}thiophene-2-sulfonamide |
| 30 | 8.6 | 5.2 | 9.8 | 5-Chloro-N-{2-ethyl-1-[1-(4-hydroxybenzyl)-1H-imidazol-2-yl]butyl}thiophene-2-sulfonamide |
| 31 | 5.3 | 26.7 | increase | N-[1-(1-Benzyl-1H-pyrrol-2-yl)-2-methylpropyl]-5-chlorothiophene-2-sulfonamide |
| 32 | 6.6 | 13.3 | increase | 5-Chloro-N-{1-[1-(4-methoxybenzyl)-1H-pyrrol-2-yl]-2-methylpropyl}thiophene-2-sulfonamide |
| 33 | ** | 2.6 | 4.3 | N-{1-[1-(Benzyloxy)-1H-pyrazol-5-yl]-2-ethylbutyl}-5-chlorothiophene-2-sulfonamide |
| 34 | — | 5.8 | 10.1 | 5-Chloro-N-{(4-fluorophenyl)[1-(4-fluorophenyl)-1H-pyrazol-5-yl]methyl}thiophene-2-sulfonamide |
| 35 | — | 12.8 | 67.2 | 5-Chloro-N-{1-[1-(4-fluorophenyl)-1H-pyrazol-5-yl]-2-phenylethyl}thiophene-2-sulfonamide |
| 36 | — | 23 | increase | 4-Chloro-N-[2-ethyl-1-(1-phenyl-1H-pyrazol-5-yl)butyl]benzenesulfonamide |

TABLE 3-continued

| Ex # | RRA data* | Aβ40 EC$_{50}$ (μM) | Aβ42 EC$_{50}$ (μM) | Name |
|---|---|---|---|---|
| 37 | — | 85.2 | increase | 4-Cyano-N-[2-ethyl-1-(1-phenyl-1H-pyrazol-5-yl)butyl]benzenesulfonamide |
| 38 | — | 13.3 | increase | 4,5-Dichloro-N-[2-ethyl-1-(1-phenyl-1H-pyrazol-5-yl)butyl]thiophene-2-sulfonamide |
| 39 | — | 25.5 | increase | 3,4-Dichloro-N-[2-ethyl-1-(1-phenyl-1H-pyrazol-5-yl)butyl]benzenesulfonamide |
| 40 | — | 4.1 | 7.5 | 5-Bromo-N-[2-ethyl-1-(1-phenyl-1H-pyrazol-5-yl)butyl]thiophene-2-sulfonamide |
| 41 | — | 21.9 | increase | 5-Chloro-N-{(1R)-1-[1-(4-fluorophenyl)-1H-pyrazol-5-yl]-2-methylpropyl}thiophene-2-sulfonamide |
| 42 | — | 1.0 | 1.0 | 5-Chloro-N-{(1S)-1-[1-(4-fluorophenyl)-1H-pyrazol-5-yl]-2-methylpropyl}thiophene-2-sulfonamide |
| 43 | — | 47.9 | increase | 4-Cyano-N-[2-ethyl-1-(1-phenyl-1H-pyrazol-5-yl)butyl]-N-methylbenzenesulfonamide |
| 44 | — | 35.7 | | 4-Chloro-N-[2-ethyl-1-(1-phenyl-1H-pyrazol-5-yl)butyl]-N-methylbenzenesulfonamide |
| 45 | — | 33.6 | increase | 4,5-Dichloro-N-[2-ethyl-1-(1-phenyl-1H-pyrazol-5-yl)butyl]-N-methylthiophene-2-sulfonamide |
| 46 | — | 70.1 | increase | 5-Chloro-N-[2-ethyl-1-(1-phenyl-1H-pyrazol-5-yl)butyl]-N-methylthiophene-2-sulfonamide |
| 47 | — | 61.2 | increase | 3,4-Dichloro-N-[2-ethyl-1-(1-phenyl-1H-pyrazol-5-yl)butyl]-N-methylbenzenesulfonamide |
| 48 | — | 65.1 | increase | 5-Bromo-N-[2-ethyl-1-(1-phenyl-1H-pyrazol-5-yl)butyl]-N-methylthiophene-2-sulfonamide |

*Fold increase of APPI, all compounds tested at 20 μg/mL.
**Inactive due to toxicity; however, this compound, at 3-4 μM, reduces Aβ levels by 50% in CHO cells transfected with human APP$_{695}$ as measured by ELISA without exhibiting toxicity.
***Inactive; however, this compound, at 1-4 μM, reduces Aβ levels by 50% in CHO cells transfected with human APP$_{695}$ as measured by ELISA without exhibiting toxicity.

All documents identified herein are incorporated by reference. It will be readily understood that numerous variations to the techniques and conditions described in the foregoing examples and description of specific embodiments can be varied without departing from the scope of the invention as defined by the following claims.

What is claimed is:

1. A compound of formula (Ia) or a pharmaceutically acceptable salt thereof, of the structure:

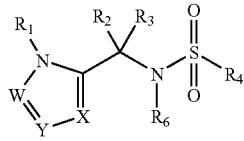

(Ia)

wherein:
R$_1$ is selected from the group consisting of lower alkyl, substituted lower alkyl, phenyl, substituted phenyl, benzyl, substituted benzyl, benzyloxy, substituted benzyloxy, and SO$_2$R$_5$;
R$_5$ is selected from the group consisting of phenyl, substituted phenyl, heterocycle, substituted heterocycle, alkyl, and substituted alkyl;
R$_2$ is selected from the group consisting of lower alkyl, substituted lower alkyl, CF$_3$, alkenyl, substituted alkenyl, alkynyl, substituted alkynyl, phenyl, substituted phenyl, and cycloalkyl;
R$_3$ is selected from the group consisting of hydrogen, lower alkyl, and substituted lower alkyl;
R$_4$ is selected from the group consisting of phenyl, substituted phenyl, heterocycle, substituted heterocycle, thiophene, and substituted thiophene;
R$_6$ is selected from the group consisting of hydrogen, lower alkyl, substituted lower alkyl, CF$_3$, alkenyl, substituted alkenyl, alkynyl, substituted alkynyl, phenyl, substituted phenyl, cycloalkyl, and substituted cycloalkyl;
W, X, and Y are selected from the group consisting of (i), (ii), and (iii):
(i) W is N, Y is CR$_7$, and X is N;
(ii) W is CR$_7$, Y is CR$_7$, and X is N; and
(iii) W is CR$_7$, Y is CR$_7$, and X is CR$_7$;
R$_7$ is selected from the group consisting of hydrogen, halogen, lower alkyl, and substituted lower alkyl.

2. The compound according to claim 1, wherein R$_1$ is substituted benzyl.

3. The compound according to claim 1, wherein R$_1$ is substituted phenyl.

4. The compound according to claim 1, wherein R$_2$ is lower alkyl.

5. The compound according to claim 2, wherein R$_3$ is hydrogen.

6. The compound according to claim 2, wherein R$_4$ is thiophene or substituted thiophene.

7. The compound according to claim 6, wherein R$_4$ is 5-chloro-2-thiophene.

8. The compound according to claim 1, wherein R$_6$ is H.

9. The compound according to claim 1 which is 5-Chloro-N-{2-ethyl-1-[1-(4-fluorobenzyl)-1H-1,2,4-triazol-5-yl]butyl}thiophene-2-sulfonamide, 5-Chloro-N-(2-ethyl-1-{1-[4-(trifluoromethoxy)benzyl]-1H-1,2,4-triazol-5-yl}butyl) thiophene-2-sulfonamide, 5-Chloro-N-{2-ethyl-1-[1-(4-methoxybenzyl)-1H-1,2,4-triazol-5-yl]butyl}thiophene-2-sulfonamide, N-[1-(1-Benzyl-1H-1,2,4-triazol-5-yl)-2- ethylbutyl]-5-chlorothiophene-2-sulfonamide, N-[1-(1-Benzyl-1H-1,2,4-triazol5-yl)-2-methylpropyl]-5-chlorothiophene-2-sulfonamide, 5-Chloro-N-{2-methyl-1-[1-(4-methylbenzyl)-1H-1,2,4-triazol-5-yl]propyl}thiophene-2-sulfonamide, N-[1-(1-Benzyl-1H-1,2,4-triazol-5-yl)ethyl]-5-chlorothiophene-2-sulfonamide, 5-Chloro-N-{1-[1-(4-methylbenzyl)-1H-1,2,4-triazol-5-yl]ethyl}thiophene-2-sulfonamide, 5-Chloro-N-{2-ethyl-1-[1-(4-methylbenzyl)-1H-1,2,4-triazol-5-yl]butyl}thiophene-2-sulfonamide, N-[1-(1-Benzyl-1H-imidazol-2-yl)-2-ethylbutyl]-5-chlorothiophene-2-sulfonamide, 5-Chloro-N-{2-ethyl-1-[1-(4-methoxybenzyl)-1H-imidazol-2-yl]butyl}thiophene-2-sulfonamide, 5-Chloro-N-{2-ethyl-1-[1-(4-hydroxybenzyl)-1-H-imidazol-2-yl]butyl}thiophene-2-sulfonamide, and N-[1-(1-Benzyl-1H-pyrrol-2-yl)-2-methylpropyl]-5-chlorothiophene-2-sulfonamide.

\* \* \* \* \*